(12) United States Patent
Sagara et al.

(10) Patent No.: US 8,889,666 B2
(45) Date of Patent: Nov. 18, 2014

(54) QUINOLYL PYRROLO PYRIMIDYL CONDENSED-RING COMPOUND AND SALT THEREOF

(71) Applicant: Taiho Pharmaceutical Co., Ltd., Tokyo (JP)

(72) Inventors: Takeshi Sagara, Tsukuba (JP); Satoru Ito, Tsukuba (JP); Sachie Otsuki, Tsukuba (JP); Katsumasa Nonoshita, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/984,299

(22) PCT Filed: Feb. 22, 2013

(86) PCT No.: PCT/JP2013/054615
§ 371 (c)(1),
(2), (4) Date: Aug. 8, 2013

(87) PCT Pub. No.: WO2013/125709
PCT Pub. Date: Aug. 29, 2013

(65) Prior Publication Data
US 2014/0057899 A1    Feb. 27, 2014

(30) Foreign Application Priority Data
Feb. 23, 2012    (JP) ................................. 2012-037565

(51) Int. Cl.
| | | |
|---|---|---|
| *A01N 43/00* | (2006.01) | |
| *A61K 31/55* | (2006.01) | |
| *C07D 471/14* | (2006.01) | |
| *C07D 487/14* | (2006.01) | |

(52) U.S. Cl.
CPC ............ *C07D 487/14* (2013.01); *C07D 471/14* (2013.01)
USPC ....... 514/214.02; 514/267; 544/250; 540/578

(58) Field of Classification Search
CPC combination set(s) only.
See application file for complete search history.

(56) References Cited

FOREIGN PATENT DOCUMENTS

| | | |
|---|---|---|
| WO | 2006/102079 A1 | 9/2006 |
| WO | 2007/075554 A2 | 7/2007 |
| WO | 2007/114926 A2 | 10/2007 |
| WO | 2008/018881 A1 | 2/2008 |
| WO | 2008/039218 A2 | 4/2008 |
| WO | 2008/121742 A2 | 10/2008 |
| WO | 2011/046964 A2 | 4/2011 |

OTHER PUBLICATIONS

Huang et al., Synthesis of cyclopropanes by Pd-catalyzed activation of alkyl C-H bonds, Tetrahedron Letters, 2009, vol. 50, No. 52, pp. 7235-7238.
Rixson et al., The development of Domino Reactions Incorporating the Heck Reaction: The Formation of N-Heterocycles, European Journal of Organic Chemistry, 2012, vol. 2012, No. 3, pp. 544-558.
PCT/ISA/220, PCT/ISA/210 and PCT/ISA/237 issued in PCT Application No. PCT/JP2014/054218 on Mar. 25, 2014, 7 pages.
Zapf et al., "Covalent Inhibitors of Interleukin-2 Inducible T Cell Kinase (Itk) with Nanomolar Potency in a Whole-Blood Assay", Journal of Medicinal Chemistry, 2012, vol. 55, No. 22, p. 10047-10063.
Lacouture, "Mechanisms of cutaneous toxicities to EGFR inhibitors", Nature Reviews Cancer, 2006, vol. 6, pp. 803-812.
Arteaga, "The Epidermal Growth Factor Receptor: From Mutant Oncogene in Nonhuman Cancers to Therapeutic Target in Human Neoplasia", Journal of Clinical Oncology, 2001, vol. 19, No. 18s, pp. 32s-40s.
World Statistics 2011, Chapter 14, 14-1, p. 332.
Doebele et al., New Strategies to overcome limitations of reversible EGFR tyrosine kinase inhibitor therapy in non-small cell lung cancer, Lung Cancer, 2010, vol. 69, pp. 1-12.
Pao et al., "Rational, biologically based treatment of EGFR-mutant non-small-cell lung cancer", Nature Reviews Cancer, 2010, Vol.10, pp. 760-774.
Japanese Search Report for PCT/JP2013/054615 dated Feb. 22, 2013, 9 pgs.

*Primary Examiner* — Wu-Cheng Winston Shen
*Assistant Examiner* — Jean Cornet
(74) *Attorney, Agent, or Firm* — Rothwell, Figg, Ernst & Manbeck, P.C.

(57) ABSTRACT

The present invention provides a new compound that has an inhibitory action against EGFR and that has cell growth inhibitory effects. The present invention further provides a pharmaceutical preparation useful for preventing and/or treating cancer, based on the EGFR inhibitory effect of the compound. A compound represented by the following Formula (I)

(I)

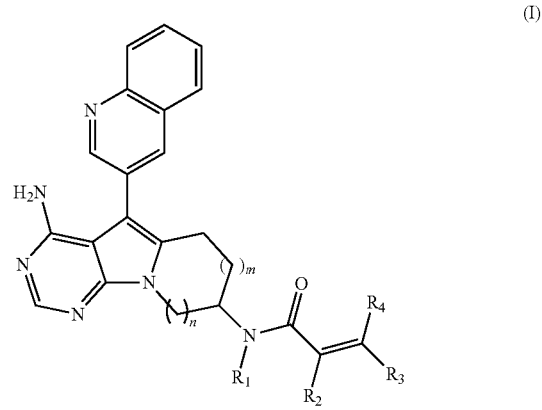

or a salt thereof.

9 Claims, No Drawings

QUINOLYL PYRROLO PYRIMIDYL CONDENSED-RING COMPOUND AND SALT THEREOF

CROSS REFERENCE TO RELATED APPLICATION

This application is a 35 U.S.C. 371 National Phase Entry Application from PCT/JP2013/054615, filed Feb. 22, 2013, which claims the benefit of Japanese Patent Application No. 2012-037565 filed Feb. 23, 2012, the disclosures of which are incorporated herein in their entirety by reference.

TECHNICAL FIELD

The present invention relates to quinolyl pyrrolo pyrimidyl condensed-ring compounds having an inhibitory action against Epidermal Growth Factor Receptor (EGFR), and pharmaceutical compositions containing those as an active ingredient.

BACKGROUND ART

EGFR is a receptor type tyrosine kinase, exerts its physiological function in normal tissue when being bound to Epidermal Growth Factor (EGF) which is a ligand, and contributes to growth, apoptosis inhibition, etc., in epithelial tissues (Non-Patent Literature (NPL) 1).

In addition, EGFR is one of the oncogenes, and amplification of the EGFR gene and high expression or mutation of its protein are seen in various cancer types such as head and neck cancer, breast cancer, colorectal cancer, esophagus cancer, pancreatic cancer, lung cancer, ovarian cancer, renal cancer, bladder cancer, skin cancer, and brain tumor (Non-Patent Literature (NPL) 2). In Japan and western countries, approximately 170 to 375 in every 100,000 people perish due to cancer every year, and cancer ranks high as a cause of death (Non-Patent Literature (NPL) 3). Above all, the death toll due to lung cancer reaches approximately 1,400,000 per year worldwide, and since non-small cell lung cancer accounts for equal to or more than 80% of lung cancers, there has been a desire for development of effective therapy for that (Non-Patent Literature (NPL) 4).

In recent years, responsible genes for these cancers are being identified, and a mutation in the EGFR gene is also one of them and results in an active mutated EGFR protein. An active mutated EGFR protein is, for example, a deletion of amino acid at positions 746-750 (EGFR (d746-750)), a mutation of amino acid at position 858 from leucine to arginine (EGFR (L858R)), or the like. Such mutations are reported, for example, in 20-40% of non-small cell lung cancer cases in Japan, and in 10-15% of non-small cell lung cancer cases in western countries. Since non-small cell lung cancer having these mutations is highly susceptible against gefitinib (product name: Iressa®) and erlotinib (product name: Tarceva®) which are chemical agents (EGFR inhibitors) that inhibit the kinase activity of EGFR, these chemical agents are used as therapeutic agents in Japan and western countries. However, the cancer acquires resistance against gefitinib and erlotinib after 6 to 12 months from the beginning of use and therapeutic effect becomes weak. Therefore, this acquired resistance has been a serious problem for treating non-small cell lung cancer having a highly-susceptible mutated EGFR. It has been revealed that approximately 50% of the acquired resistance is due to emergence of a resistant mutated EGFR protein (EGFR (d746-750/T790M) or EGFR (T790M/L858R)) having a second mutation in the EGFR gene resulting in amino acid at position 790 to change from threonine to methionine. It has been an important task to develop a therapeutic agent that is effective against non-small cell lung cancer having this drug resistant mutated EGFR (Non-Patent Literature (NPL) 5).

On the other hand, skin abnormality and alimentary canal disorder are reported as common side effects of the EGFR inhibitors of gefitinib and erlotinib, which are clinically used as therapeutic agents at present, and of EGFR inhibitors such as BIBW2992 etc., which are under clinical trial. It is widely thought that these side effects are caused by the EGFR inhibitors inhibiting the activity of not only a mutated EGFR expressed in non-small cell lung cancer, but also the activity of the wild-type EGFR (EGFR (WT)) expressed in the skin or alimentary canal (Non-Patent Literature (NPL) 1). From a standpoint of side effect reduction, it is considered to be preferable to have a weak inhibitory activity against EGFR (WT) in normal tissues.

Thus, there is expectation of possibly suppressing growth of non-small cell lung cancer cells having a drug resistant mutated EGFR through administration of a chemical agent having weaker inhibitory activity against the wild-type EGFR when compared to inhibitory activity against the drug resistant mutated EGFR whose amino acid at position 790 has mutated to methionine, at an administration dose where the side effect to the skin or alimentary canal does not appear strongly. This is predicted to contribute to treating the cancer, and prolonging life and improving QOL of patients. In addition, if the chemical agent has weak inhibitory activity against the wild-type EGFR but has strong in inhibitory activity not only against drug resistant mutated EGFR but also against highly-susceptible mutated EGFRs such as the EGFR (d746-750) and the EGFR (L858R) etc., which are highly susceptible against gefitinib and erlotinib; there is expectation of possibly suppressing growth of non-small cell lung cancer cells expressing a highly-susceptible mutated EGFR or a drug resistant mutated EGFR at an administration dose where the side effect to the skin or alimentary canal does not appear strongly, or expectation of possibly reducing the frequency of drug resistant mutated EGFR that emerges, as acquired resistance, from non-small cell lung cancer cells expressing a highly-susceptible mutated EGFR. This is predicted to contribute to treating the cancer, and prolonging life and improving QOL of patients. Furthermore, since expressions of highly-susceptible mutated EGFR and drug resistant mutated EGFR can be used in the actual scene of therapy as indices for stratification to enable selection of patients, they contribute greatly from an ethical viewpoint.

As a compound having a structure analogous to a compound according to present invention, N-(3-(4-amino-6,7,8,9-tetrahydropyrimido[5,4-b]indolizin-5-yl)phenyl)benzamide derivative is known (Patent Literature (PTL) 1). Although Patent Literature 1 describes using the amide compound for treating diseases characterized by B-RAF kinase, the Literature does not disclose specific tests and results therefrom corroborating a kinase inhibiting activity, and such activity is not confirmed.

CITATION LIST

Patent Literature

PTL 1: International Publication No. WO2006/102079 pamphlet

Non-Patent Literature

NPL 1: Nature Rev. Cancer, vol. 6, pp 803-811 (2006)
NPL 2: J. Clin. Oncol., vol. 19, 32s-40s (2001)

NPL 3: Ministry of Internal Affairs and Communications Statistics Bureau homepage/statistical data/world statistics "World Statistics 2011" Chapter 14 People's Life and Social Security, 14-1 Death Rates by Causes Death NPL 4: Lung Cancer, vol. 69, pp 1-12 (2010)

NPL 5: Nature Rev. Cancer, vol. 10, pp 760-774 (2010)

SUMMARY OF INVENTION

Technical Problem

As described above, EGFR inhibitors, although expected to be effective in cancer therapy, are currently not clinically effective enough.

Therefore, an object of the present invention is to provide a new compound that strongly inhibits EGFR, or a salt thereof. A further object of the present invention is to provide: a new compound that inhibits EGFR (d746-750), EGFR (L858R), EGFR (d746-750/T790M), and EGFR (T790M/L858R), but does not inhibit EGFR (WT); or a salt thereof.

Solution to Problem

The present inventors have conducted thorough research in order to achieve the above described object. As a result, they have found that a group of quinolyl pyrrolo pyrimidyl condensed-ring compounds of the present invention have excellent inhibitory activity against EGFR and have cancer-cell-growth inhibitory action, and are useful as medication for treating cancer, and thereby they have achieved the present invention.

Thus, the present invention provides the following items.

Item 1. A compound represented by the following Formula (I) or a salt thereof.

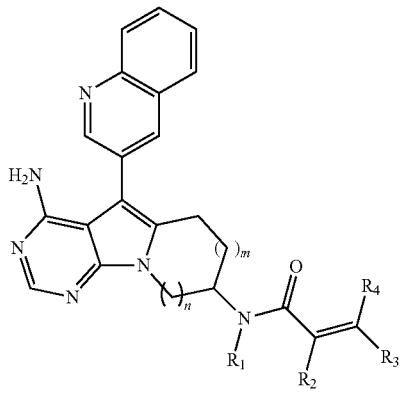

(I)

(In the formula, m is 1 or 2;

n is 1 or 2;

$R_1$ is a hydrogen atom or a $C_1$-$C_4$ alkyl group; and $R_2$, $R_3$, and $R_4$ are the same or different, and are each a hydrogen atom, a halogen atom, a $C_1$-$C_4$ alkyl group, or a group represented by Formula (a):

 (a)

(in the formula, $R_5$ and $R_6$ are the same or different and each represents a hydrogen atom or a $C_1$-$C_4$ alkyl group, or $R_5$ and $R_6$ may form a heterocycloalkyl group having a 4 to 6 membered-ring, together with the nitrogen atom bound thereto)).

Item 2. The compound or a salt thereof according to item 1, wherein m is 1 or 2;

n is 1 or 2;

$R_1$ is a hydrogen atom or a $C_1$-$C_4$ alkyl group; and $R_2$, $R_3$, and $R_4$ are the same or different, and are each a hydrogen atom, a halogen atom, a $C_1$-$C_4$ alkyl group, or a group represented by Formula (a):

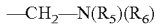 (a)

(in the formula, $R_5$ and $R_6$ are the same or different and each represents a $C_1$-$C_4$ alkyl group).

Item 3. The compound or a salt thereof according to item 1 or 2, wherein m is 1 or 2;

n is 1 or 2;

$R_1$ is a hydrogen atom or methyl group; and $R_2$, $R_3$, and $R_4$ are the same or different, and are each a hydrogen atom, a chlorine atom, or a dimethylamino methyl group.

Item 4. The compound or a salt thereof according to any one of items 1 to 3, wherein m and n are (m,n)=(1,1), (1,2), or (2,1).

Item 5. The compound or a salt thereof according to any one of items 1 to 4, wherein the compound is selected from the following group of compounds.

(R)-N-(4-amino-5-(quinolin-3-yl)-6,7,8,9-tetrahydropyrimido[5,4-b]indolizin-8-yl)acrylamide (S)-N-(4-amino-5-(quinolin-3-yl)-6,7,8,9-tetrahydropyrimido[5,4-b]indolizin-8-yl)acrylamide N-(4-amino-5-(quinolin-3-yl)-6,7,8,9-tetrahydropyrimido[5,4-b]indolizin-8-yl)-N-methylacrylamide (E)-N-(4-amino-5-(quinolin-3-yl)-6,7,8,9-tetrahydropyrimido[5,4-b]indolizin-8-yl)-4-(dimethylamino)-2-butenamide (S,E)-N-(4-amino-5-(quinolin-3-yl)-6,7,8,9-tetrahydropyrimido[5,4-b]indolizin-8-yl)-3-chloroacrylamide (S,Z)—N-(4-amino-5-(quinolin-3-yl)-6,7,8,9-tetrahydropyrimido[5,4-b]indolizin-8-yl)-3-chloroacrylamide (S)-N-(4-amino-5-(quinolin-3-yl)-7,8,9,10-tetrahydro-6H-pyrimido[5',4':4,5]pyrrolo[1,2-a]azepin-8-yl)acrylamide (S)-N-(4-amino-5-(quinolin-3-yl)-7,8,9,10-tetrahydro-6H-pyrimido[5',4':4,5]pyrrolo[1,2-a]azepin-9-yl)acrylamide (R)-N-(4-amino-5-(quinolin-3-yl)-7,8,9,10-tetrahydro-6H-pyrimido[5',4':4,5]pyrrolo[1,2-a]azepin-9-yl)acrylamide Item 6. An EGFR inhibitor comprising the compound or a salt thereof according to any one of items 1 to 5 as an active ingredient.

Item 7. A pharmaceutical composition comprising the compound or a salt thereof according to any one of items 1 to 5.

Item 8. An antitumor agent comprising the compound or a salt thereof according to any one of items 1 to 5 as an active ingredient.

Item 9. A method for treating or preventing cancer, the method comprising a step of administering, to a mammal, the compound or a salt thereof according to any one of items 1 to 5 at a dose effective for treating or preventing cancer.

Item 10. Use of the compound or a salt thereof according to any one of items 1 to 5 in the manufacture of an antitumor agent.

Item 11. The compound or a salt thereof according to any one of items 1 to 5 for use in the treatment or prevention of cancer.

The present invention also provides a method for producing synthetic intermediates of the compound of the present invention specified in the following items.

Item 12. A method for producing a compound represented by formula (VIII), or a salt thereof, the method comprising the steps of:

[I] causing an organoborane reagent to act on a compound represented by formula (VII), or a salt thereof

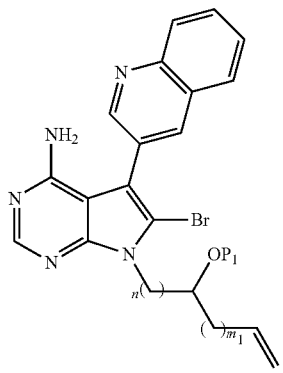

(VII)

(in the formula, $P_1$ is a protecting group of a hydroxy group, n is 1 or 2, and $m_1$ is 0 or 1); and

[II] causing intramolecular cyclization to occur in a reaction product of the step [I] with usage of a palladium(0) catalyst and in the presence of an alkali metal hydroxide.

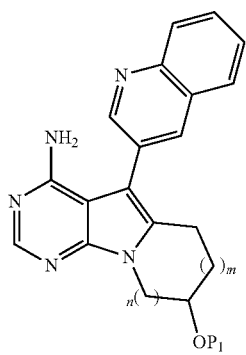

(VIII)

(In the formula, m is 1 or 2, and $P_1$ and n are as described above).

Item 13. A method for producing a compound represented by formula (XX) or a salt thereof, (XX)

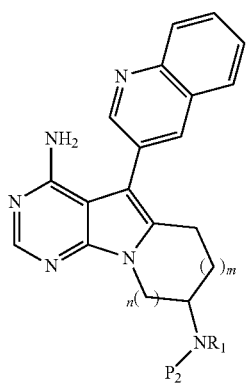

(in the formula, $R_1$ is a hydrogen atom or a $C_1$-$C_4$ alkyl group, $P_2$ is a protecting group of an amino group, m is 1 or 2, and n is 1 or 2)

the method comprising the steps of:

[I] causing an organoborane reagent to act on a compound represented by formula (XIX), or a salt thereof

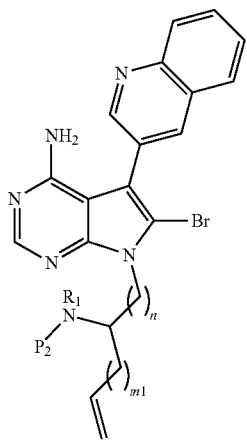

(XIX)

(in the formula, $R_1$, $P_2$, and n are as described above, and $m_1$ is 0 or 1); and

[II] causing intramolecular cyclization to occur in a reaction product of the step [I] with usage of a palladium(0) catalyst and in the presence of an alkali metal hydroxide.

Advantageous Effects of Invention

According to the present invention, a new compound represented by Formula (I) described above or a salt thereof useful as an EGFR inhibitor is provided.

It is clear that the compound of the present invention or a salt thereof has excellent EGFR inhibition activity and a growth suppression effect against cancer cell lines. In addition, the compound or a salt thereof has an advantage of having small side effects since having excellent selectivity against EGFRs. Therefore, the compound or a salt thereof of the present invention is useful as an agent for treating and/or preventing cancer.

DESCRIPTION OF EMBODIMENTS

The compound of Formula (I) according to the present invention is a quinolyl pyrrolo pyrimidyl condensed-ring compound that has a quinoline structure and an α,β-unsaturated amide structure, and is thus a novel compound nowhere disclosed in any of the above-mentioned prior art documents, etc.

Specifically, the compound specifically disclosed in PTL 1 is an N-(3-(4-amino-6,7,8,9-tetrahydropyrimido[5,4-b]indolizin-5-yl)phenyl)benzamide derivative. The compound of the present invention is different from the compound disclosed in PTL 1 in that the compound of the present invention has a quinoline structure and an α,β-unsaturated amide structure.

In the present specification, the term "$C_1$-$C_4$ alkyl" refers to a straight or branched alkyl group having 1 to 4 carbon atoms. Specific examples thereof include methyl, ethyl, n-propyl, isopropyl, n-butyl, isobutyl, sec-butyl, tert-butyl, and the like.

In this specification, examples of the "halogen" include chlorine, bromine, fluorine, and iodine.

In this specification, the term "4 to 6 membered heterocycloalkyl" refers to a 4 to 6 membered cycloalkyl group having 1 to 2 nitrogen atoms in the ring. Specific examples thereof include azetidinyl, pyrrolidinyl, piperidyl, imidazolidinyl, and the like.

m and n in Formula (I) are preferably (m,n)=(1,1), (1,2), or (2,1).

$R_1$ in Formula (I) is preferably hydrogen or methyl.

$R_2$, $R_3$, and $R_4$ in Formula (I) may be the same or different, and each preferably represents hydrogen, halogen, $C_1$-$C_4$ alkyl, or a group represented by the above Formula (a). When at least one of $R_2$, $R_3$, and $R_4$ in Formula (I) is a group represented by Formula (a), each of $R_5$ and $R_6$ is preferably $C_1$-$C_4$ alkyl, and both of $R_5$ and $R_6$ are more preferably methyl.

$R_2$ in Formula (I) is more preferably hydrogen.

$R_3$ in Formula (I) is more preferably hydrogen, chlorine, or dimethylaminomethyl.

$R_4$ in Formula (I) is more preferably hydrogen or chlorine.

In the present invention, the compound of Formula (I) wherein m is 1 or 2; n is 1 or 2; $R_1$ is hydrogen or methyl; $R_2$, $R_3$, and $R_4$ are the same or different and represent hydrogen, chlorine, or dimethylaminomethyl, or a salt thereof, is preferable.

When m is 1 and n is 1, the compound of Formula (I) wherein $R_1$ is hydrogen or methyl; $R_2$ is hydrogen; one of $R_3$ and $R_4$ is hydrogen, chlorine, or dimethylaminomethyl, and the other is hydrogen; or a salt thereof, is preferable.

When m=1 and n=2 or m=2 and n=1, the compound of Formula (I) wherein all of $R_1$, $R_2$, $R_3$, and $R_4$ are hydrogen or a salt thereof is preferable.

Specific examples of preferable compounds of the present invention include the following:
(R)-N-(4-amino-5-(quinolin-3-yl)-6,7,8,9-tetrahydropyrimido[5,4-b]indolizin-8-yl)acrylamide;
(S)-N-(4-amino-5-(quinolin-3-yl)-6,7,8,9-tetrahydropyrimido[5,4-b]indolizin-8-yl)acrylamide;
N-(4-amino-5-(quinolin-3-yl)-6,7,8,9-tetrahydropyrimido[5,4-b]indolizin-8-yl)-N-methylacrylamide;
(E)-N-(4-amino-5-(quinolin-3-yl)-6,7,8,9-tetrahydropyrimido[5,4-b]indolizin-8-yl)-4-(dimethylamino)-2-butenamide;
(S,E)-N-(4-amino-5-(quinolin-3-yl)-6,7,8,9-tetrahydropyrimido[5,4-b]indolizin-8-yl)-3-chloroacrylamide;
(S,Z)—N-(4-amino-5-(quinolin-3-yl)-6,7,8,9-tetrahydropyrimido[5,4-b]indolizin-8-yl)-3-chloroacrylamide;
(S)-N-(4-amino-5-(quinolin-3-yl)-7,8,9,10-tetrahydro-6H-pyrimido[5',4':4,5]pyrrolo[1,2-a]azepin-8-yl)acrylamide;
(S)-N-(4-amino-5-(quinolin-3-yl)-7,8,9,10-tetrahydro-6H-pyrimido[5',4':4,5]pyrrolo[1,2-a]azepin-9-yl)acrylamide; and
(R)-N-(4-amino-5-(quinolin-3-yl)-7,8,9,10-tetrahydro-6H-pyrimido[5',4':4,5]pyrrolo[1,2-a]azepin-9-yl)acrylamide.

Compounds that have potent enzyme inhibitory activity against EGFR (T790M/L858R) are preferable, and compounds with an enzyme inhibitory activity of 2 nM or less are more preferable. Compounds that have potent enzyme inhibitory activity against EGFR (d746-750/T790M) are preferable, and compounds with an enzyme inhibitory activity of 2 nM or less are more preferable.

Next, the method for producing the compound according to the present invention will be explained:

Compound (I) of the present invention can be produced, for example, by the following production methods or the methods described in Examples. However, the method for producing Compound (I) of the present invention is not limited to these reaction examples.

Production Method 1

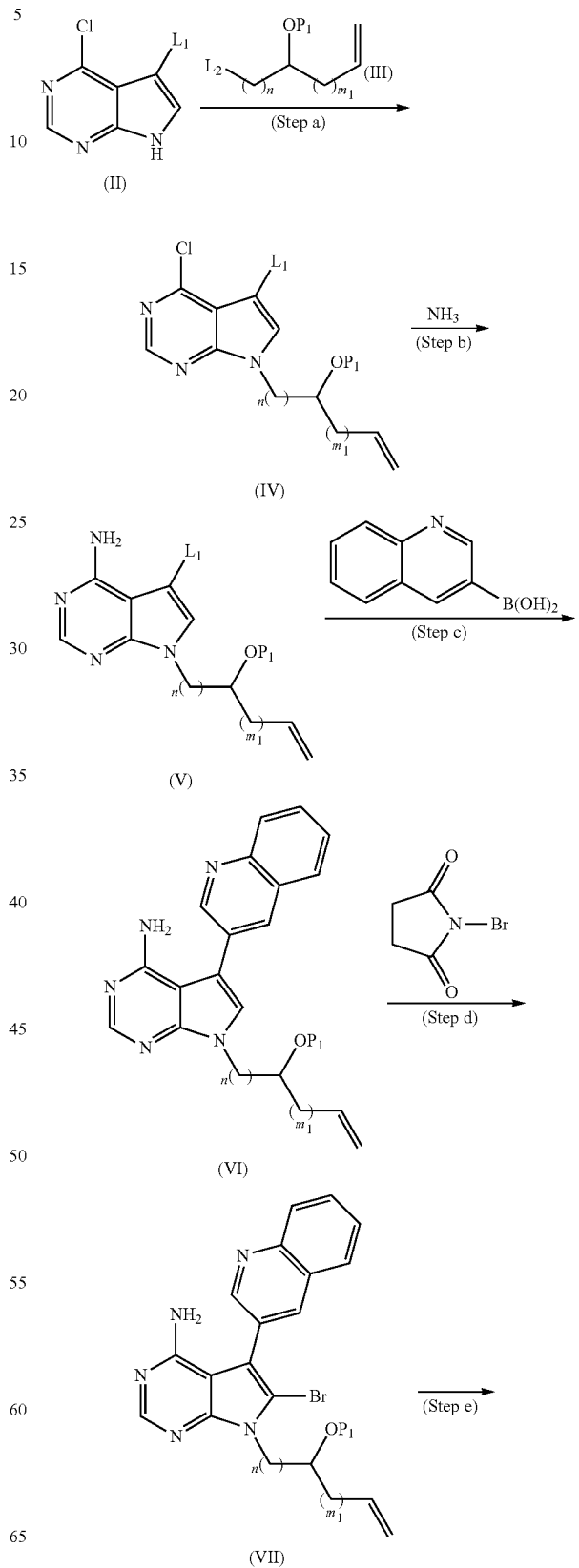

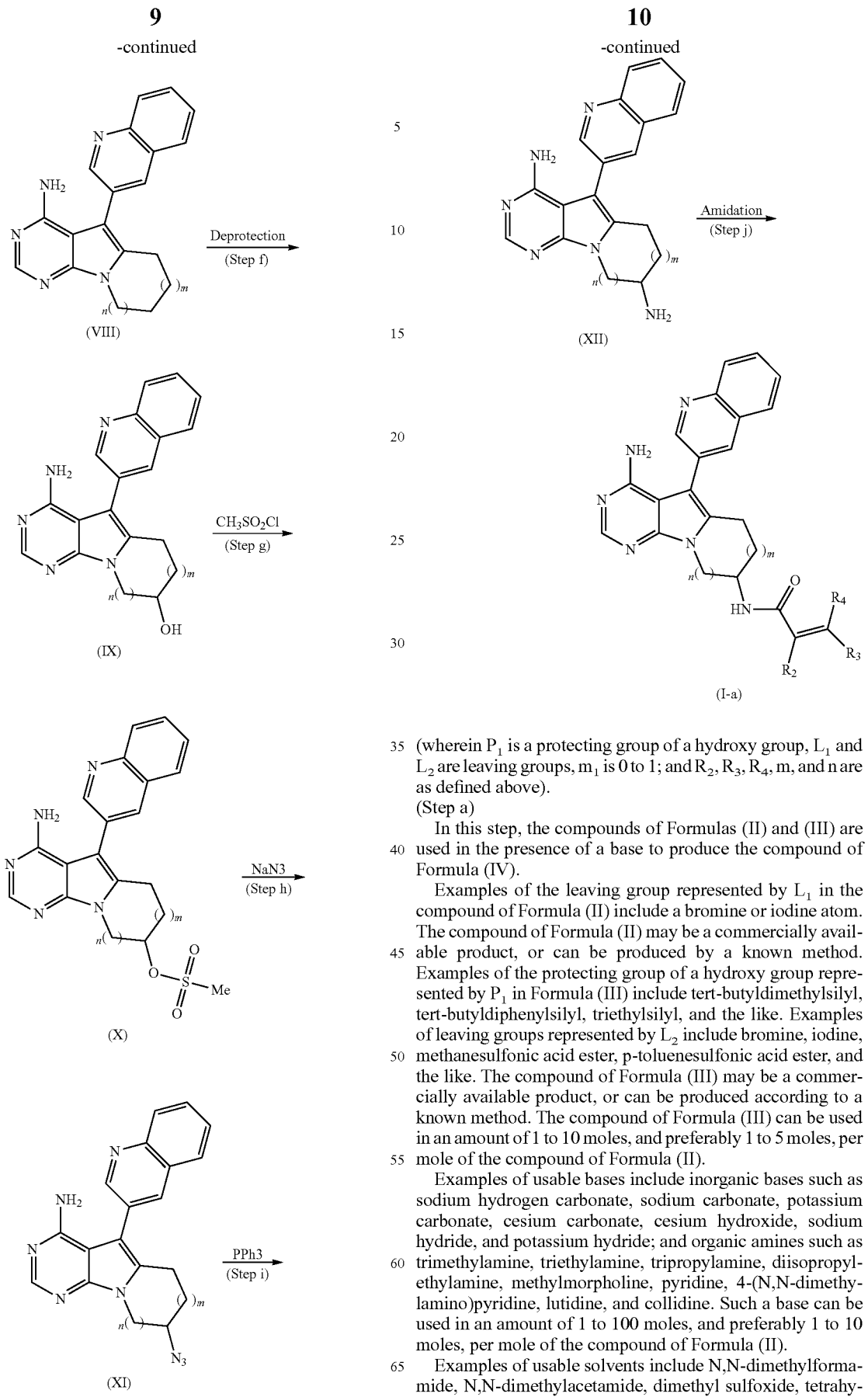

(wherein $P_1$ is a protecting group of a hydroxy group, $L_1$ and $L_2$ are leaving groups, $m_1$ is 0 to 1; and $R_2$, $R_3$, $R_4$, m, and n are as defined above).

(Step a)

In this step, the compounds of Formulas (II) and (III) are used in the presence of a base to produce the compound of Formula (IV).

Examples of the leaving group represented by $L_1$ in the compound of Formula (II) include a bromine or iodine atom. The compound of Formula (II) may be a commercially available product, or can be produced by a known method. Examples of the protecting group of a hydroxy group represented by $P_1$ in Formula (III) include tert-butyldimethylsilyl, tert-butyldiphenylsilyl, triethylsilyl, and the like. Examples of leaving groups represented by $L_2$ include bromine, iodine, methanesulfonic acid ester, p-toluenesulfonic acid ester, and the like. The compound of Formula (III) may be a commercially available product, or can be produced according to a known method. The compound of Formula (III) can be used in an amount of 1 to 10 moles, and preferably 1 to 5 moles, per mole of the compound of Formula (II).

Examples of usable bases include inorganic bases such as sodium hydrogen carbonate, sodium carbonate, potassium carbonate, cesium carbonate, cesium hydroxide, sodium hydride, and potassium hydride; and organic amines such as trimethylamine, triethylamine, tripropylamine, diisopropylethylamine, methylmorpholine, pyridine, 4-(N,N-dimethylamino)pyridine, lutidine, and collidine. Such a base can be used in an amount of 1 to 100 moles, and preferably 1 to 10 moles, per mole of the compound of Formula (II).

Examples of usable solvents include N,N-dimethylformamide, N,N-dimethylacetamide, dimethyl sulfoxide, tetrahydrofuran, 1,4-dioxane, N-methylpyrrolidin-2-one, acetonitrile, and the like. Such solvents can be used singly, or as a mixture. The reaction time is 0.1 to 100 hours, and preferably 0.5 to 24 hours. The reaction temperature is 0° C. to the boiling temperature of the solvent, and preferably 0 to 100° C.

The thus-obtained compound of Formula (IV) can be subjected to the subsequent step after or without isolation or purification by known separation and purification means, such as concentration, vacuum concentration, crystallization, solvent extraction, reprecipitation, and chromatography.

(Step b)

In this step, the compound of Formula (IV) is reacted with ammonia or a salt thereof to produce the compound of Formula (V).

The amount of ammonia or a salt thereof used in this step is typically an equimolar to excessive molar amount per mole of the compound of Formula (IV).

Any reaction solvent that does not adversely affect the reaction can be used. Examples of usable reaction solvents include water, methanol, ethanol, isopropanol, tert-butyl alcohol, tetrahydrofuran, 1,2-dimethoxyethane, 1,4-dioxane, N,N-dimethylformamide, N-methylpyrrolidin-2-one, dimethyl sulfoxide, and mixed solvents thereof.

The reaction temperature is typically 0 to 200° C., and preferably room temperature to 150° C. The reaction time is typically 5 minutes to 7 days, and preferably 30 minutes to 24 hours.

The thus-obtained compound of Formula (V) can be subjected to the subsequent step after or without isolation and purification by known separation and purification means, such as concentration, vacuum concentration, crystallization, solvent extraction, reprecipitation, and chromatography.

(Step c)

In this step, the compound of Formula (V) is subjected to a coupling reaction with 3-quinolineboronic acid or 3-quinolineboronic acid ester to produce the compound of Formula (VI).

This step can be performed according to a generally known method (for example, Chemical Reviews, Vol. 95, p. 2457, 1995). For example, this step can be performed in the presence of a transition metal catalyst and a base in a solvent that does not adversely affect the reaction.

The amount of 3-quinolineboronic acid or 3-quinolineboronic acid ester used may be 1 to 10 moles, and preferably 1 to 3 moles, per mole of the compound of Formula (V).

Examples of transition metal catalysts include palladium catalysts (e.g., palladium acetate, palladium chloride, tetrakistriphenylphosphine palladium, 1,1'-bis(diphenylphosphino)ferrocene-palladium (II)dichloride, and tris(dibenzylideneacetone)dipalladium(0)), nickel catalysts (e.g., nickel chloride), and the like. If necessary, a ligand (e.g., triphenylphosphine, tri-tert-butylphosphine, or 2-dicyclohexylphosphino-2',4',6'-triisopropylbiphenyl) can be added, and a metal oxide (such as copper oxide or silver oxide) can be used as a cocatalyst. The amount of the transition metal catalyst used may vary depending on the type of catalyst. The transition metal catalyst is typically used in an amount of 0.0001 to 1 mole, and preferably 0.01 to 0.5 moles, per mole of the compound of Formula (V). The amount of the ligand used is typically 0.0001 to 4 moles, and preferably 0.01 to 2 moles, per mole of the compound of Formula (V). The amount of the cocatalyst used is typically 0.0001 to 4 moles, and preferably 0.01 to 2 moles, per mole of the compound of Formula (V).

Examples of usable bases include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkali metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), alkali metal alkoxides (e.g., sodium methoxide, sodium ethoxide, sodium tert-butoxide, and potassium tert-butoxide), alkali metal disilazides (e.g., lithium disilazide, sodium disilazide, and potassium disilazide), and the like. Among them, alkali metal salts such as sodium carbonate, potassium carbonate, cesium carbonate, sodium phosphate, and potassium phosphate; alkali metal alkoxides such as sodium tert-butoxide and potassium tert-butoxide; and organic amines such as triethylamine and diisopropylethylamine are preferable. The amount of the base used is typically 0.1 to 10 moles, and preferably 1 to 5 moles, per mole of the compound of Formula (V).

Any solvent that does not adversely affect the reaction can be used. Examples of usable solvents include hydrocarbons (e.g., benzene, toluene, and xylene), halogenated hydrocarbons (e.g., chloroform and 1,2-dichloroethane), nitriles (e.g., acetonitrile), ethers (e.g., 1,2-dimethoxyethane, tetrahydrofuran, and 1,4-dioxane), alcohols (e.g., methanol and ethanol), aprotic polar solvents (e.g., N,N-dimethylformamide, dimethyl sulfoxide, and hexamethyl phosphoryl amide), water, and mixed solvents thereof. The reaction time is 0.1 to 100 hours, and preferably 0.5 to 24 hours. The reaction temperature is 0° C. to the boiling temperature of the solvent, and preferably 20 to 150° C.

The thus-obtained compound of Formula (VI) can be subjected to the subsequent step after or without isolation and purification by known separation and purification means, such as concentration, vacuum concentration, crystallization, solvent extraction, reprecipitation, and chromatography.

(Step d)

In this step, Compound (VI) is brominated with N-bromosuccinimide to produce Compound (VII).

The halogenation can be performed by the method disclosed in WO 2006/102079, or by a method similar thereto.

The amount of N-bromosuccinimide used in this step is 0.5 to 2.0 moles, and preferably 0.9 to 1.2 moles, per mole of the compound of Formula (VI).

Any reaction solvent that does not adversely affect the reaction can be used. For example, tetrahydrofuran, 1,4-dioxane, N,N-dimethylformamide, N-methylpyrrolidin-2-one, or a mixed solvent thereof can be preferably used.

The reaction temperature is typically −20 to 50° C., and preferably 0° C. to room temperature. The reaction time is typically 1 minute to 2 days, and preferably 5 minutes to 12 hours.

The thus-obtained compound of Formula (VII) can be subjected to the subsequent step after or without isolation or purification by known separation and purification means, such as concentration, vacuum concentration, crystallization, solvent extraction, reprecipitation, and chromatography.

(Step e)

In this step, an organic borane reagent is allowed to act on the compound of Formula (VII) to prepare an alkyl borane intermediate in the system, and the intermediate is converted to a compound of Formula (VIII) in the presence of a transition metal catalyst and a base.

This step can be performed according to a generally known method (for example, WO 2006/102079).

Examples of organic borane reagents include 9-BBN(9-borabicyclo[3.3.1]-nonane), 9-BBN(9-borabicyclo[3.3.1]-nonane)dimer, disiamylborane(bis(1,2-dimethylpropyl)borane), thexylborane(1,1,2-trimethylpropyl)borane), and the like. The organic borane reagent is preferably 9-BBN(9-borabicyclo[3.3.1]-nonane) or 9-BBN(9-borabicyclo[3.3.1]- nonane)dimer, and particularly preferably 9-BBN(9-borabicyclo[3.3.1]-nonane). The amount of the organic borane reagent used is not particularly limited insofar as an alkyl borane intermediate can be produced. The organic borane reagent can be used in an amount of 1 to 20 moles per mole of the compound of Formula (VII); the amount of the organic borane reagent is preferably 6 to 10 moles from the viewpoint of facilitating the progress of the reaction.

As a transition metal catalyst, for example, a bivalent palladium catalyst (e.g., palladium acetate, palladium chloride, and 1,1'-bis(diphenylphosphino)ferrocene-palladium (II) dichloride) can be used. If necessary, a ligand (e.g., triphenylphosphine and tri-tert-butylphosphine) can be used. The amount of the transition metal catalyst used may vary depending on the type of catalyst. The transition metal catalyst is typically used in an amount of 0.0001 to 1 mole, and preferably 0.01 to 0.5 moles, per mole of the compound of Formula (VII). The ligand is typically used in an amount of 0.0001 to 4 moles, and preferably 0.01 to 2 moles, per mole of the compound of Formula (VII).

Alternatively, for example, a zerovalent palladium catalyst can be used. Examples of zerovalent palladium catalysts include tetrakistriphenylphosphine palladium (0), tris(dibenzylideneacetone)dipalladium (0), palladium carbon (0), and the like. Tetrakistriphenylphosphine palladium (0) or tris (dibenzylideneacetone)dipalladium (0) is preferable, and tetrakistriphenylphosphine palladium (0) is particularly preferable. The amount of the zerovalent palladium catalyst used is not particularly limited insofar as the intramolecular cyclization reaction can proceed, and may vary depending on the type of catalyst. The zerovalent palladium catalyst can be used in an amount of 0.0001 to 1 mole, and preferably 0.01 to 0.5 moles, per mole of the compound of Formula (VII).

If necessary, a ligand may be added with a zerovalent palladium catalyst. Examples of such ligands include triphenylphosphine, 1,1'-bis(diphenylphosphino)ferrocene, tri-tert-butylphosphine, tricyclohexylphosphine, 2-dicyclohexylphosphino-2',6'-dimethoxybiphenyl, 2-dicyclohexylphosphino-2',4',6'-triisopropylbiphenyl, 2-(di-tert-butylphosphino)biphenyl, 2-dicyclohexylphosphino-2'-(N,N-dimethylamino)biphenyl, 4,5'-bis(diphenylphosphino)-9,9'-dimethylxanthene, and the like. When tris(dibenzylideneacetone)dipalladium (0) is used as a zerovalent palladium catalyst, triphenylphosphine can be added as a ligand. The amount of the ligand used is not particularly limited insofar as the intramolecular cyclization reaction can proceed. The ligand can be used in an amount of 0.0001 to 4 moles, and preferably 0.01 to 2 moles, per mole of the compound of Formula (VII).

Examples of bases include inorganic bases such as sodium hydrogen carbonate, sodium carbonate, potassium carbonate, cesium carbonate, and alkali metal hydroxides. Alkali metal hydroxides are preferable. Examples of alkali metal hydroxides include lithium hydroxide, sodium hydroxide, potassium hydroxide, and cesium hydroxide. Lithium hydroxide, sodium hydroxide, potassium hydroxide, or cesium hydroxide is preferably used. Lithium hydroxide or sodium hydroxide is particularly preferable. The amount of the base used is not particularly limited insofar as the reaction proceeds. The base can be used in an amount of 1 to 100 moles, and preferably 2 to 20 moles, per mole of the compound of Formula (VII). Alkali metal hydroxide can be used in the form of an aqueous alkali metal hydroxide solution.

As the combination of an organic borane reagent, an alkali metal hydroxide, and a zerovalent palladium catalyst, a combination of a preferable organic borane reagent, a preferable alkali metal hydroxide, and a preferable zerovalent palladium catalyst is preferable. A combination of a particularly preferable organic borane reagent, a particularly preferable alkali metal hydroxide, and a particularly preferable zerovalent palladium catalyst is particularly preferable.

Any solvent that does not adversely affect the reaction can be used. Examples thereof include hydrocarbons (e.g., benzene, toluene, and xylene), ethers (e.g., 1,2-dimethoxyethane, tetrahydrofuran, and 1,4-dioxane), aprotic polar solvents (e.g., N,N-dimethylformamide, dimethyl sulfoxide, and hexamethyl phosphoryl amide), water, and mixtures thereof. 1,2-Dimethoxyethane or tetrahydrofuran is preferably used. Tetrahydrofuran is particularly preferable from the viewpoint of stability of the organic borane reagent and the generated alkylborane intermediate. The amount of the solvent used is not particularly limited insofar as the reaction proceeds. The solvent can be used in an amount that is 1 to 300 times, and preferably 10 to 96 times, the weight of the compound of Formula (VII).

The reaction time is not particularly limited insofar as the compound of Formula (VIII) can be obtained. The reaction time may be 0.1 to 100 hours, and preferably 0.5 to 24 hours.

The reaction temperature is not particularly limited insofar as the compound of Formula (VIII) can ultimately be obtained. The reaction temperature may be −20° C. to the boiling temperature of the solvent, and preferably 0 to 150° C. In the intramolecular cyclization reaction of the alkylborane intermediate using a zerovalent palladium catalyst and an alkali metal hydroxide aqueous solution, a low reaction temperature tends to cause side reactions, which results in a low yield. Therefore, the temperature is preferably 61° C. or higher.

The thus-obtained compound of Formula (VIII) can be subjected to the subsequent step after or without isolation and purification by known separation and purification means, such as concentration, vacuum concentration, crystallization, solvent extraction, reprecipitation, and chromatography.

In this step, generation of an alkylborane intermediate in the system can be confirmed. For example, LCMS spectra can be used as the confirmation method.

(Step f)

In this step, the protected hydroxy group of the compound of Formula (VIII) is deprotected to produce the compound of Formula (IX).

The deprotection can be performed by a known method, such as the method described in Protective Groups in Organic Synthesis, T. W. Greene, John Wiley & Sons (1981); or a method similar thereto.

When tert-butyldimethylsilyl is used as a protecting group, tetrabutyl ammonium fluoride is used as a deprotection reagent. The amount of the reagent used is preferably 1 to 10 moles per mole of the compound of (VIII).

Any solvent that does not adversely affect the reaction can be used. Examples of usable solvents include ethers (e.g., 1,2-dimethoxyethane and tetrahydrofuran), aprotic polar solvents (e.g., N,N-dimethylformamide, dimethyl sulfoxide, and hexamethyl phosphoryl amide), and mixed solvents thereof. The reaction time is 0.1 to 100 hours, and preferably 0.5 to 24 hours. The reaction temperature is 0 to 80° C., and preferably 0 to 50° C.

The thus-obtained compound of Formula (IX) can be subjected to the subsequent step after or without isolation and purification by known separation and purification means, such as concentration, vacuum concentration, crystallization, solvent extraction, reprecipitation, and chromatography.

(Step g)

In this step, methanesulfonyl chloride is allowed to act on the compound of Formula (IX) to produce the compound of Formula (X).

The amount of methanesulfonyl chloride used may be 1 to 5 moles, and more preferably 1 to 2 moles, per mole of the compound of Formula (IX).

Examples of usable bases include organic amines such as trimethylamine, triethylamine, tripropylamine, diisopropylethylamine, N-methylmorpholine, pyridine, 4-(N,N-dimethylamino)pyridine, lutidine, and collidine. Such a base can be used in an amount of 1 to 10 moles, and preferably 1 to 5 moles, per mole of the compound of Formula (IX).

Any solvent that does not adversely affect the reaction can be used. Examples of usable solvents include hydrocarbons (e.g., benzene, toluene, and xylene), halogenated hydrocarbons (e.g., chloroform and 1,2-dichloroethane), nitriles (e.g., acetonitrile), ethers (e.g., 1,2-dimethoxyethane, tetrahydrofuran, and 1,4-dioxane), alcohols (e.g., methanol and ethanol), aprotic polar solvents (e.g., N,N-dimethylformamide, dimethyl sulfoxide, and hexamethylphosphoramide), and mixed solvents thereof. The reaction time is 0.1 to 24 hours, and preferably 0.1 to 12 hours. The reaction temperature is $-20°$ C. to the boiling temperature of the solvent, and preferably $0°$ C. to room temperature.

The thus-obtained compound of Formula (X) can be subjected to the subsequent step after or without isolation or purification by known separation and purification means, such as concentration, vacuum concentration, crystallization, solvent extraction, reprecipitation, and chromatography.

(Step h)

In this step, sodium azide is allowed to act on the compound of Formula (X) to produce the compound of Formula (XI).

The sodium azide can be used in an amount of 1 to 10 moles, and preferably 1 to 5 moles, per mole of the compound of Formula (X).

Any solvent that does not adversely affect the reaction can be used. Examples of usable solvents include N,N-dimethylformamide, dimethyl sulfoxide, hexamethyl phosphoryl amide, and mixed solvents thereof. The reaction time is 0.1 to 24 hours, and preferably 0.5 to 12 hours. The reaction temperature is room temperature to the boiling temperature of the solvent, and preferably 50 to 100° C.

The thus-obtained compound of Formula (XI) can be subjected to the subsequent step after or without isolation or purification by known separation and purification means, such as concentration, vacuum concentration, crystallization, solvent extraction, reprecipitation, and chromatography.

(Step i)

In this step, the compound of Formula (XI) is reacted in the presence of triphenylphosphine in an aqueous solvent to produce the compound of Formula (XII).

The triphenylphosphine may be a commonly used reagent or a solid-supported reagent. The amount of triphenylphosphine used may be 1 to 10 moles, and preferably 1 to 5 moles, per mole of the compound of Formula (XI).

Any solvent that does not adversely affect the reaction can be used. Examples of usable solvents include tetrahydrofuran/water, 1,4-dioxane/water, and the like. The reaction time is 0.1 to 24 hours, and preferably 0.5 to 12 hours. The reaction temperature is room temperature to the boiling temperature of the solvent, and preferably 50° C. to the boiling temperature of the solvent.

The thus-obtained compound of Formula (XII) can be subjected to the subsequent step after or without isolation or purification by known separation and purification means, such as concentration, vacuum concentration, crystallization, solvent extraction, reprecipitation, and chromatography.

(Step j)

In this step, the compound of Formula (XII) is amidated with an $\alpha,\beta$-unsaturated carboxylic acid or an $\alpha,\beta$-unsaturated acid chloride or bromide to produce the compound of Formula (I-a) according to the present invention.

When a carboxylic acid is used as an amidation reagent, the carboxylic acid can be used in an amount of 0.5 to 10 moles, preferably 1 to 3 moles, per mole of the compound of Formula (XII), in the presence of a suitable condensing agent. The carboxylic acid may be a commercially available product, or can be produced according to a known method.

Any reaction solvent that does not adversely affect the reaction can be used. Examples of usable solvents include toluene, benzene, methylene chloride, chloroform, tetrahydrofuran, 1,4-dioxane, N,N-dimethylformamide, dimethylacetamide, N-methylpyrrolidin-2-one, dimethyl sulfoxide, and mixed solvents thereof. The reaction temperature is typically $-78$ to $200°$ C., and preferably 0 to $50°$ C. The reaction time is typically 5 minutes to 3 days, and preferably 5 minutes to 10 hours.

Examples of condensation agents include diphenylphosphoryl azide, N,N'-dicyclohexylcarbodiimide, benzotriazol-1-yloxy-trisdimethylaminophosphonium salts, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, 0-(7-azabenzotriazo-1-yl)-N,N,N',N'-tetramethylhexauronium hexafluorophosphate, and the like.

If necessary, a base can be optionally added for the reaction. Examples of usable bases include organic bases such as triethylamine, diisopropylethylamine, pyridine, lutidine, collidine, 4-(N,N-dimethylamino)pyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base can be added in an amount of 1 to 100 moles, and preferably 1 to 10 moles, per mole of the compound of Formula (XII).

When an acid chloride or acid bromide is used as an amidation reagent, the acid halide is used in an amount of 0.5 to 5 moles, and preferably 0.9 to 1.1 moles, per mole of the compound of Formula (XII). The acid halide may be a commercially available product, or can be produced according to a known method.

Any reaction solvent that does not adversely affect the reaction can be used. Examples thereof include toluene, benzene, methylene chloride, chloroform, tetrahydrofuran, 1,4-dioxane, N,N-dimethylformamide, dimethylacetamide, N-methylpyrrolidin-2-one, acetonitrile, water, and mixed solvents thereof. The reaction temperature is typically $-78$ to $200°$ C., preferably 0 to $50°$ C. The reaction time is typically 5 minutes to 3 days, and preferably 5 minutes to 10 hours.

If necessary, a base can be added for the reaction. Examples of usable bases include organic bases such as triethylamine, diisopropylethylamine, pyridine, lutidine, collidine, 4-(N,N-dimethylamino)pyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base can be added in an amount of 1 to 100 moles, and preferably 1 to 20 moles, per mole of the compound of Formula (XII).

The thus-obtained compound of Formula (I-a) can be isolated and purified by known separation and purification means, such as concentration, vacuum concentration, crystallization, solvent extraction, reprecipitation, and chromatography.

[Chem. 7]
Production Method 2

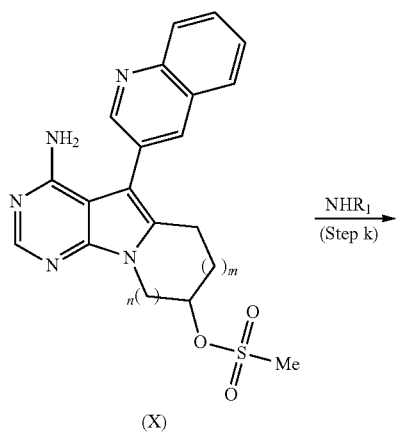

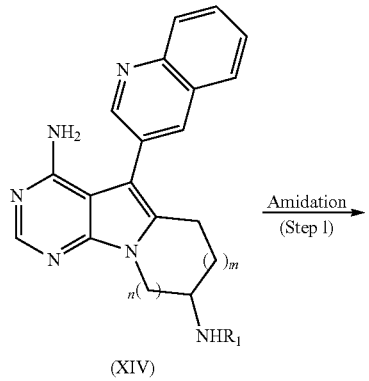

(wherein $R_1$, $R_2$, $R_3$, $R_4$, m, and n are as defined above).

(Step k)

In this step, an alkylamine is allowed to react on the compound of Formula (X) to produce the compound of Formula (XIV).

The amount of the alkylamine used is 2 moles to an excess molar amount per mole of the compound of Formula (X).

Any solvent that does not adversely affect the reaction can be used. Examples thereof include hydrocarbons (e.g., benzene, toluene, and xylene), halogenated hydrocarbons (e.g., chloroform and 1,2-dichloroethane), nitriles (e.g., acetonitrile), ethers (e.g., 1,2-dimethoxyethane, tetrahydrofuran, and 1,4-dioxane), aprotic polar solvents (e.g., N,N-dimethylformamide, dimethyl sulfoxide, and hexamethyl phosphoryl amide), and mixed solvents thereof. The reaction time is 0.1 to 100 hours, and preferably 1 to 24 hours. The reaction temperature is room temperature to the boiling temperature of the solvent, and preferably 50° C. to the boiling temperature of the solvent.

The thus-obtained compound of Formula (XIV) can be subjected to the subsequent step after or without isolation or purification by known separation and purification means, such as concentration, vacuum concentration, crystallization, solvent extraction, reprecipitation, and chromatography.

(Step l)

This step can be performed in the same manner as in step j.

Production Method 3

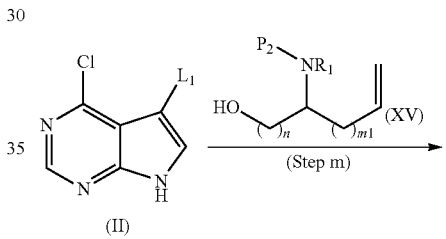

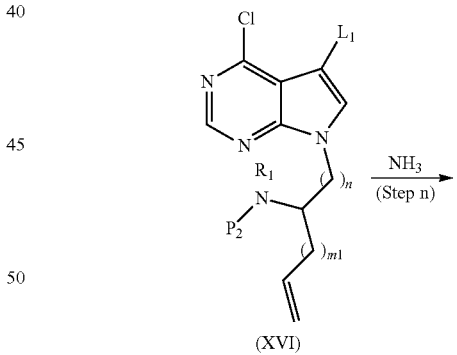

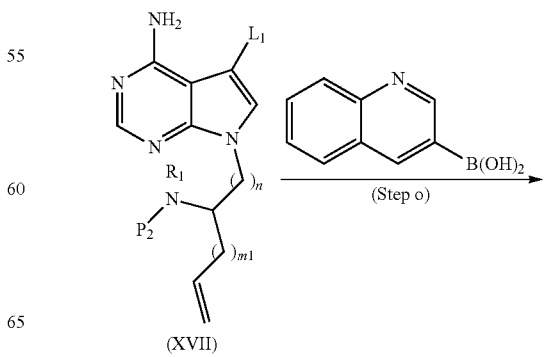

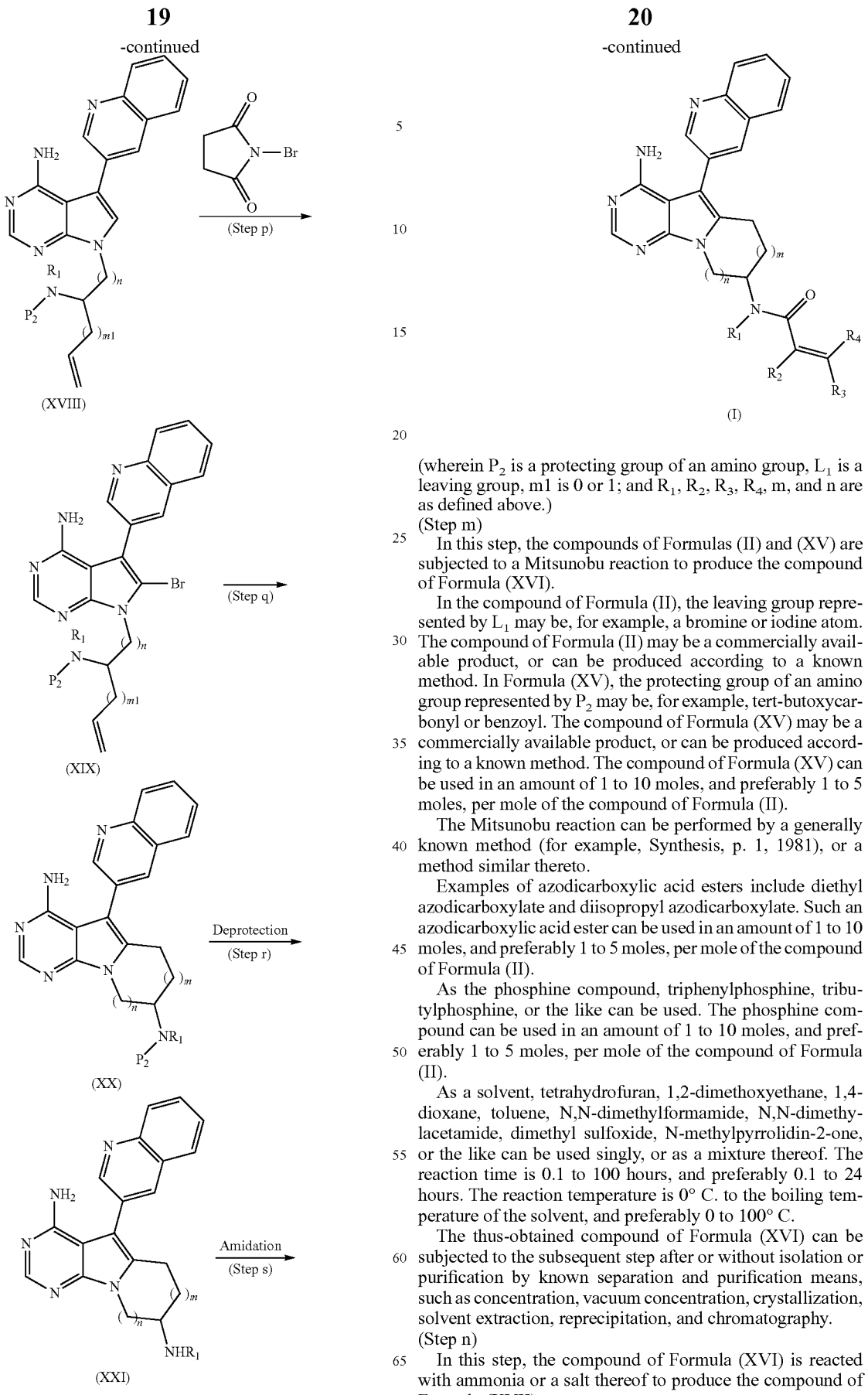

(wherein $P_2$ is a protecting group of an amino group, $L_1$ is a leaving group, m1 is 0 or 1; and $R_1$, $R_2$, $R_3$, $R_4$, m, and n are as defined above.)

(Step m)

In this step, the compounds of Formulas (II) and (XV) are subjected to a Mitsunobu reaction to produce the compound of Formula (XVI).

In the compound of Formula (II), the leaving group represented by $L_1$ may be, for example, a bromine or iodine atom. The compound of Formula (II) may be a commercially available product, or can be produced according to a known method. In Formula (XV), the protecting group of an amino group represented by $P_2$ may be, for example, tert-butoxycarbonyl or benzoyl. The compound of Formula (XV) may be a commercially available product, or can be produced according to a known method. The compound of Formula (XV) can be used in an amount of 1 to 10 moles, and preferably 1 to 5 moles, per mole of the compound of Formula (II).

The Mitsunobu reaction can be performed by a generally known method (for example, Synthesis, p. 1, 1981), or a method similar thereto.

Examples of azodicarboxylic acid esters include diethyl azodicarboxylate and diisopropyl azodicarboxylate. Such an azodicarboxylic acid ester can be used in an amount of 1 to 10 moles, and preferably 1 to 5 moles, per mole of the compound of Formula (II).

As the phosphine compound, triphenylphosphine, tributylphosphine, or the like can be used. The phosphine compound can be used in an amount of 1 to 10 moles, and preferably 1 to 5 moles, per mole of the compound of Formula (II).

As a solvent, tetrahydrofuran, 1,2-dimethoxyethane, 1,4-dioxane, toluene, N,N-dimethylformamide, N,N-dimethylacetamide, dimethyl sulfoxide, N-methylpyrrolidin-2-one, or the like can be used singly, or as a mixture thereof. The reaction time is 0.1 to 100 hours, and preferably 0.1 to 24 hours. The reaction temperature is 0° C. to the boiling temperature of the solvent, and preferably 0 to 100° C.

The thus-obtained compound of Formula (XVI) can be subjected to the subsequent step after or without isolation or purification by known separation and purification means, such as concentration, vacuum concentration, crystallization, solvent extraction, reprecipitation, and chromatography.

(Step n)

In this step, the compound of Formula (XVI) is reacted with ammonia or a salt thereof to produce the compound of Formula (XVII).

This step can be performed in the same manner as in step b.

The thus-obtained compound of Formula (XVII) can be subjected to the subsequent step after or without isolation or purification by known separation and purification means, such as concentration, vacuum concentration, crystallization, solvent extraction, reprecipitation, and chromatography.

(Step o)

In this step, the compound of Formula (XVII) is subjected to a coupling reaction with 3-quinolineboronic acid or a 3-quinolineboronic acid ester to produce the compound of Formula (XVIII).

This step can be performed in the same manner as in step c.

The thus-obtained compound of Formula (XVIII) can be subjected to the subsequent step after or without isolation or purification by known separation and purification means, such as concentration, vacuum concentration, crystallization, solvent extraction, reprecipitation, and chromatography.

(Step p)

In this step, Compound (XVIII) is brominated with N-bromosuccinimide to produce the compound of Formula (XIX).

This step can be performed in the same manner as in step d. The thus-obtained compound of Formula (XIX) can be subjected to the subsequent step after or without isolation or purification by known separation and purification means, such as concentration, vacuum concentration, crystallization, solvent extraction, reprecipitation, and chromatography.

(Step q)

In this step, after an organic borane reagent is allowed to act on the compound of Formula (XIX) and an alkylborane intermediate is produced in the system, the compound of Formula (XX) is produced in the presence of a transition metal catalyst and a base.

This step can be performed according to a generally known method (for example, WO2006/102079).

Examples of organic borane reagents include 9-BBN(9-borabicyclo[3.3.1]-nonane), 9-BBN (9-borabicyclo[3.3.1]-nonane)dimer, disiamylborane(bis(1,2-dimethylpropyl)borane), thexylborane((1,1,2-trimethylpropyl)borane), and the like. 9-BBN(9-borabicyclo[3.3.1]-nonane) or 9-BBN (9-borabicyclo[3.3.1]-nonane)dimer are preferably used. 9-BBN (9-borabicyclo[3.3.1]-nonane) is particularly preferable. The amount of the organic borane reagent used is not particularly limited, insofar as an alkylborane intermediate is produced. The organic borane reagent can be used in an amount of 1 to 20 moles per mole of the compound of Formula (XIX). In view of facilitating the progress of the reaction, the amount of the organic borane reagent is preferably 6 to 10 moles per mole of the compound of Formula (XIX).

Examples of transition metal catalysts include bivalent palladium catalysts (e.g., palladium acetate, palladium chloride, and 1,1'-bis(diphenylphosphino)ferrocene-palladium (II)dichloride). If necessary, a ligand (e.g., triphenylphosphine and tri-tert-butylphosphine) can be added. The amount of the transition metal catalyst used may vary depending on the type of catalyst. The transition metal catalyst is typically used in an amount of 0.0001 to 1 mole, and preferably 0.01 to 0.5 moles, per mole of the compound of Formula (XIX). The amount of the ligand used is typically 0.0001 to 4 moles, and preferably 0.01 to 2 moles, per mole of the compound of Formula (XIX).

As a transition metal catalyst, for example, a zerovalent palladium catalyst can also be used. Examples of usable zerovalent palladium catalysts include tetrakistriphenylphosphine palladium (0), tris(dibenzylideneacetone)dipalladium (0), and palladium carbon (0). Tetrakistriphenylphosphine palladium (0) or tris(dibenzylideneacetone)dipalladium (0) is preferably used. Tetrakistriphenylphosphine palladium (0) is particularly preferable. The amount of the zerovalent palladium catalyst used is not particularly limited insofar as the intramolecular cyclization reaction can proceed. The amount of the zerovalent palladium catalyst used may vary depending on the type of catalyst. The zerovalent palladium catalyst can be used in an amount of 0.0001 to 1 mole, and preferably 0.01 to 0.5 moles, per mole of the compound of Formula (XIX).

If necessary, a ligand can be further added with a zerovalent palladium catalyst. Examples of such ligands include triphenylphosphine, 1,1'-bis(diphenylphosphino)ferrocene, tri-tert-butylphosphine, tricyclohexylphosphine, 2-dicyclohexylphosphino-2',6'-dimethoxybiphenyl, 2-dicyclohexylphosphino-2',4',6'-triisopropylbiphenyl, 2-(di-tert-butylphosphino)biphenyl, 2-dicyclohexylphosphino-2'-(N,N-dimethylamino)biphenyl, 4,5'-bis(diphenylphosphino)-9,9'-dimethylxanthene, and the like. When tris(dibenzylideneacetone)dipalladium (0) is used as a zerovalent palladium catalyst, triphenylphosphine can be added as a ligand. The amount of the ligand used is not particularly limited insofar as the intramolecular cyclization reaction can proceed. The ligand can be used in an amount of 0.0001 to 4 moles, and preferably 0.01 to 2 moles, per mole of the compound of Formula (XIX).

Examples of bases include inorganic bases such as sodium hydrogen carbonate, sodium carbonate, potassium carbonate, cesium carbonate, and alkali metal hydroxides. Alkali metal hydroxides are preferable. Examples of alkali metal hydroxides include lithium hydroxide, sodium hydroxide, potassium hydroxide, cesium hydroxide, and the like. Lithium hydroxide, sodium hydroxide, potassium hydroxide, or cesium hydroxide is preferably used. Lithium hydroxide or sodium hydroxide is particularly preferable. The amount of the base used is not particularly limited insofar as the reaction proceeds. The base can be used in an amount of 1 to 100 moles, and preferably 2 to 20 moles, per mole of the compound of Formula (XIX). The alkali metal hydroxide can be used in the form of an aqueous alkali metal hydroxide solution.

As the combination of an organic borane reagent, an alkali metal hydroxide, and a zerovalent palladium catalyst, a combination of a preferable organic borane reagent, a preferable alkali metal hydroxide, and a preferable zerovalent palladium catalyst is preferable. A combination of a particularly preferable organic borane reagent, a particularly preferable alkali metal hydroxide, and a particularly preferable zerovalent palladium catalyst is particularly preferable.

Any solvent that does not adversely affect the reaction can be used. Examples thereof include hydrocarbons (e.g., benzene, toluene, and xylene), ethers (e.g., 1,2-dimethoxyethane, tetrahydrofuran, and 1,4-dioxane), aprotic polar solvents (e.g., N,N-dimethylformamide, dimethyl sulfoxide, and hexamethyl phosphoryl amide), water, and mixtures thereof. 1,2-dimethoxyethane or tetrahydrofuran is preferably used. Tetrahydrofuran is particularly preferable from the viewpoint of stability of the organic borane reagent and the generated alkylborane intermediate. The amount of the solvent used is not particularly limited insofar as the reaction proceeds. The solvent can be used in an amount that is 1 to 300 times, and preferably 10 to 96 times, the weight of the compound of Formula (XIX).

The reaction time is not particularly limited insofar as the compound of Formula (XX) can be obtained. The reaction time may be 0.1 to 100 hours, and preferably 0.5 to 24 hours.

The reaction temperature is not particularly limited insofar as the compound of Formula (XX) can finally be obtained. The reaction temperature may be −20° C. to the boiling temperature of the solvent, and preferably 0 to 150° C. In the intramolecular cyclization reaction of the alkylborane intermediate using a zerovalent palladium catalyst and an alkali metal hydroxide aqueous solution, a low reaction temperature tends to cause side reactions, which results in a low yield. Therefore, the temperature is preferably 61° C. or higher.

The thus-obtained compound of Formula (XX) can be subjected to the subsequent step after or without isolation and purification by known separation and purification means, such as concentration, vacuum concentration, crystallization, solvent extraction, reprecipitation, and chromatography.

In this step, generation of an alkylborane intermediate in the system may be confirmed. For example, LCMS spectra can be used as the confirmation method.

(Step r)

In this step, the protected amino group of the compound of Formula (XX) is deprotected to produce the compound of Formula (XXI).

The deprotection can be performed by a known method, such as the method described in Protective Groups in Organic Synthesis, T. W. Greene, John Wiley & Sons (1981); or a method similar thereto.

When tert-butoxycarbonyl is used as a protecting group, hydrochloric acid, sulfuric acid, methanesulfonic acid, trifluoroacetic acid, or the like can be used as a deprotection reagent. The reagent is preferably used in an amount of 1 to 100 moles per mole of Compound (XX).

Any solvent that does not adversely affect the reaction can be used. Examples of usable solvents include water, methanol, ethanol, methylene chloride, chloroform, and mixed solvents thereof. The reaction time is 0.1 to 100 hours, and preferably 0.5 to 24 hours. The reaction temperature is 0° C. to the boiling point of the solvent.

The thus-obtained compound of Formula (XXI) can be subjected to the subsequent step after or without isolation and purification by known separation and purification means, such as concentration, vacuum concentration, crystallization, solvent extraction, reprecipitation, and chromatography.

(Step s)

This step can be performed in the same manner as in step j.

In the above production methods 1 to 3, for functional groups having an active proton, such as amino, imino, hydroxy, carboxy, carbonyl, and amide groups, and indole, protected reagents can be used or a protecting group is introduced into such a functional group according to a usual method, and then the protecting group can be removed in an appropriate step in each production method.

The "protecting group of an amino group or protecting group of an imino group" is not particularly limited, insofar as it has a protecting function. Examples of such protecting groups include aralkyl groups such as benzyl, p-methoxybenzyl, 3,4-dimethoxybenzyl, o-nitrobenzyl, p-nitrobenzyl, benzhydryl, trityl, and cumyl; lower alkanoyl groups such as formyl, acetyl, propionyl, butyryl, pivaloyl, trifluoroacetyl, and trichloroacetyl; benzoyl; arylalkanoyl groups such as phenylacetyl and phenoxyacetyl; lower alkoxycarbonyl groups such as methoxycarbonyl, ethoxycarbonyl, propyloxycarbonyl, and tert-butoxycarbonyl; aralkyloxycarbonyl groups such as p-nitrobenzyloxycarbonyl and phenethyloxycarbonyl; lower alkylsilyl groups such as trimethylsilyl and tert-butyldimethylsilyl; tetrahydropyranyl; trimethylsilylethoxymethyl; lower alkylsulfonyl groups such as methylsulfonyl, ethylsulfonyl, and tert-butylsulfonyl; lower alkylsulfinyl groups such as tert-butylsulfinyl; arylsulfonyl groups such as benzenesulfonyl and toluenesulfonyl; and imido groups such as phthalimido. In particular, trifluoroacetyl, acetyl, tert-butoxycarbonyl, benzyloxycarbonyl, trimethylsilylethoxymethyl, cumyl, and the like are preferable.

The "protecting group of a hydroxy group" is not particularly limited insofar as it has a protecting function. Examples of such protecting groups include lower alkyl groups such as methyl, ethyl, propyl, isopropyl, and tert-butyl; lower alkylsilyl groups such as trimethylsilyl and tert-butyldimethylsilyl; lower alkoxymethyl groups such as methoxymethyl and 2-methoxyethoxymethyl; tetrahydropyranyl; trimethylsilylethoxymethyl; aralkyl groups such as benzyl, p-methoxybenzyl, 2,3-dimethoxybenzyl, o-nitrobenzyl, p-nitrobenzyl, and trityl; and acyl groups such as formyl, acetyl, and trifluoroacetyl. In particular, methyl, methoxymethyl, tetrahydropyranyl, trimethylsilylethoxymethyl, tert-butyldimethylsilyl, and acetyl are preferable.

The "protecting group of a carboxy group" is not particularly limited insofar as it has a protecting function. Examples of such protecting groups include lower alkyl groups such as methyl, ethyl, propyl, isopropyl, and tert-butyl; halo-loweralkyl groups such as 2,2,2-trichloroethyl; lower alkenyl groups such as allyl; trimethylsilylethoxymethyl; and aralkyl groups such as benzyl, p-methoxybenzyl, p-nitrobenzyl, benzhydryl, and trityl. In particular, methyl, ethyl, tert-butyl, allyl, benzyl, p-methoxybenzyl, trimethylsilylethoxymethyl, and the like are preferable.

The "protecting group of a carbonyl group" is not particularly limited insofar as it has a protecting function. Examples of such protecting groups include ethylene ketal, trimethylene ketal, dimethyl ketal, and like ketals and acetals.

The method for removing such a protecting group may vary depending on the type of protecting group, stability of the desired compound (I), etc. For example, the following methods can be used: solvolysis using an acid or a base according to the method disclosed in a publication (Protective Groups in Organic Synthesis, third edition, T. W. Green, John Wiley & Sons (1999)) or a method similar thereto, i.e., a method comprising reacting with 0.01 moles or a large excess of an acid, preferably trifluoroacetic acid, formic acid, or hydrochloric acid, or an equimolar to large excessive molar amount of a base, preferably potassium hydroxide or calcium hydroxide; chemical reduction using a metal hydride complex, etc.; or catalytic reduction using a palladium-carbon catalyst, Raney nickel catalyst, etc.

The compound of the present invention can be isolated and purified by usual isolation and purification means. Examples of such means include solvent extraction, recrystallization, preparative reversed-phase high-performance liquid chromatography, column chromatography, preparative thin-layer chromatography, and the like.

When the compound of the present invention has isomers such as optical isomers, stereoisomers, regioisomers, and rotational isomers, any of the isomers and mixtures thereof is included within the scope of the compound of the present invention. For example, when the compound has optical isomers, the optical isomer separated from a racemic mixture is also included within the scope of the compound of the present invention. Each of such isomers can be obtained as a single compound by known synthesis and separation means (e.g., concentration, solvent extraction, column chromatography, recrystallization, etc.).

In the present invention, the carbon atom bound to a substituent represented by —$NR_1$—(C=O)—$CR_2$=C($R_3$)$R_4$ in Formula (I) is an asymmetric carbon; therefore, the compound includes isomers. As stated above, unless otherwise specified, the compound of the present invention includes all of the enantiomers and mixtures thereof. The compound of the present invention may be a mixture of R and S enantiomers. Such a mixture may be a mixture comprising 90% or more, 95% or more, or 99% or more of R enantiomer; or a mixture comprising 90% or more, 95% or more, or 99% or more of S enantiomer.

Methods for chiral resolution include, for example: diastereomer method of causing a chiral resolving agent to act on the compound of the present invention to form a salt, and resolving one of the enantiomers using a solubility difference etc., of the obtained salt; preferential crystallization method of adding one of the enantiomers to a supersaturated solution of a racemate as a seed for crystallization; and column chromatography such as HPLC using a chiral column. A chiral resolving agent that can be used in the diastereomer method can be appropriately selected from, for example, acid resolving agents such as tartaric acid, malic acid, lactic acid, mandelic acid, 10-camphorsulfonic acid, and derivatives thereof; and basic resolving agents such as brucine, strychnine, quinine, and like alkaloid compounds, amino acid derivatives, cinchonidine, and α-methylbenzylamine. In addition, one of the enantiomers of the compound of the present invention alone can be obtained not only by obtaining the compound of the present invention as a mixture of each of the enantiomers and then conducting the above described methods of chiral resolution, but also by obtaining, through chiral resolution by the above described methods etc., and using one enantiomer of the compound of the present invention as a synthetic raw material. Furthermore, methods for obtaining one of the enantiomers of the compound of the present invention or its raw material compound include a method of preferentially obtaining one of the enantiomers by adjusting reaction conditions for a catalyst or the like in a reaction step of generating asymmetric carbon.

The compound or a salt thereof of the present invention may be in the form of crystals. Single crystals and polymorphic mixtures are included within the scope of the compound or a salt thereof of the present invention. Such crystals can be produced by crystallization according to a crystallization method known per se in the art. The compound or a salt thereof of the present invention may be a solvate (e.g., a hydrate) or a non-solvate. Any of such forms are included within the scope of the compound or a salt thereof of the present invention. Compounds labeled with an isotope (e.g., 3H, 14C, 35S, and 125I) are also included within the scope of the compound or a salt thereof of the present invention.

The salt of the compound of the present invention or of the intermediate thereof refers to a common salt used in the field of organic chemistry. Examples of such salts include base addition salts to carboxy when the compound has carboxy, and acid addition salts to an amino or basic heterocyclic group when the compound has an amino or basic heterocyclic group.

Examples of base addition salts include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts such as hydrochlorides, sulfates, nitrates, phosphates, and perchlorates; organic acid salts such as acetates, formates, maleates, fumarates, tartrates, citrates, ascorbates, and trifluoroacetates; and sulfonates such as methanesulfonates, isethionates, benzenesulfonates, and p-toluenesulfonates.

The compound or a salt thereof of the present invention has excellent EGFR inhibitory activity and is useful as an antitumor agent. Further, the compound or a salt thereof of the present invention has excellent selectivity toward EGFR, and advantageously fewer side effects caused by other kinases. Although the target cancer is not particularly limited, examples thereof are head and neck cancer, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, blood cancer, multiple myeloma, skin cancer, brain tumor, and mesothelioma. Preferably, the target cancer is head and neck cancer, gastric cancer, colon cancer, rectum cancer, liver cancer, pancreatic cancer, lung cancer, breast cancer, ovarian cancer, renal cancer, or prostate cancer. Lung cancer is particularly preferable.

When the compound or a salt thereof of the present invention is used as a pharmaceutical preparation, a pharmaceutical carrier can be added, if required, thereby forming a suitable dosage form according to prevention and treatment purposes. Examples of the dosage form include oral preparations, injections, suppositories, ointments, patches, and the like. Of these, oral preparations are preferable. Such dosage forms can be formed by methods conventionally known to persons skilled in the art.

As the pharmaceutical carrier, various conventional organic or inorganic carrier materials used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, pharmaceutical preparation additives, such as antiseptics, antioxidants, colorants, sweeteners, and stabilizers, may also be used, if required.

Oral solid preparations are prepared as follows. After an excipient is added optionally with a binder, disintegrant, lubricant, colorant, taste-masking or flavoring agent, etc., to the compound of the present invention, the resulting mixture is formulated into tablets, coated tablets, granules, powders, capsules, or the like by ordinary methods.

Examples of excipients include lactose, sucrose, D-mannitol, glucose, starch, calcium carbonate, kaolin, microcrystalline cellulose, and silicic acid anhydride. Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, polyvinylpyrrolidone, and the like. Examples of disintegrators include dry starch, sodium alginate, powdered agar, sodium hydrogen carbonate, calcium carbonate, sodium lauryl sulfate, stearic acid monoglyceride, lactose, and the like. Examples of lubricants include purified talc, stearic acid salt sodium, magnesium stearate, borax, polyethylene glycol, and the like. Examples of colorants include titanium oxide, iron oxide, and the like. Examples of taste-masking or flavoring agents include sucrose, bitter orange peel, citric acid, tartaric acid, and the like.

When a liquid preparation for oral administration is prepared, a taste-masking agent, a buffer, a stabilizer, a flavoring agent, and the like may be added to the compound of the present invention; and the resulting mixture may be formulated into an oral liquid preparation, syrup, elixir, etc., according to an ordinary method.

In this case, the same taste-masking or flavoring agent as those mentioned above may be used. An example of the buffer is sodium citrate, and examples of the stabilizer include tragacanth, gum arabic, and gelatin. As necessary, these preparations for oral administration may be coated according to methods known in the art with an enteric coating or other coating for the purpose of, for example, persistence of effects. Examples of such coating agents include hydroxypropyl methylcellulose, ethyl cellulose, hydroxymethyl cellulose, hydroxypropyl cellulose, polyoxyethylene glycol, and Tween 80®.

When an injection agent is prepared, a pH regulator, a buffer, a stabilizer, an isotonizing agent, a local anesthetic, and the like, may be added to the compound of the present invention; and the mixture may be formulated into a subcutaneous, intramuscular, or intravenous injection according to an ordinary method.

Examples of the pH adjuster and the buffer used herein include sodium citrate, sodium acetate, and sodium phosphate. Examples of the stabilizer include sodium pyrosulfite, EDTA, thioglycolic acid, and thiolactic acid. Examples of the local anesthetic include procaine hydrochloride and lidocaine hydrochloride. Examples of the tonicity agent include sodium chloride, dextrose, D-mannitol, and glycerol.

When a suppository is prepared, pharmaceutically acceptable carriers known in the art, such as polyethylene glycol, lanolin, cacao butter, and fatty acid triglyceride; and as necessary, surfactants such as Tween 80 ®, may be added to the compound of the present invention, and the resulting mixture may be formulated into a suppository according to an ordinary method.

When an ointment is prepared, a commonly used base, stabilizer, wetting agent, preservative, and the like, may be blended into the compound of the present invention, as necessary; and the obtained mixture may be mixed and formulated into an ointment according to an ordinary method.

Examples of the base include liquid paraffin, white petrolatum, white beeswax, octyl dodecyl alcohol, and paraffin.

Examples of the preservative include methyl paraoxybenzoate, ethyl paraoxybenzoate, and propyl paraoxybenzoate.

When a patch is prepared, the above-described ointment, cream, gel, paste, or the like, may be applied to an ordinary substrate according to an ordinary method.

As the substrate, woven fabrics or non-woven fabrics comprising cotton, staple fibers, or chemical fibers; and films or foam sheets of soft vinyl chloride, polyethylene, polyurethane, etc., are suitable.

The amount of the compound of the present invention to be incorporated in each of such dosage unit forms depends on the condition of the patient to whom the compound is administered, the dosage form thereof, etc. In general, in the case of an oral agent, the amount of the compound is 0.05 to 1000 mg per dosage unit form. In the case of an injection, the amount of the compound is 0.01 to 500 mg per dosage unit form; and in the case of a suppository, the amount of the compound is 1 to 1000 mg per dosage unit form.

The daily dose of the medicine in such a dosage form depends on the condition, body weight, age, gender, etc., of the patient, and cannot be generalized. For example, the daily dose for an adult (body weight: 50 kg) may be generally 0.05 to 5,000 mg, and preferably 0.1 to 1,000 mg; and is preferably administered in one dose, or in two to three divided doses, per day.

Examples of mammals to which the compound of the present invention is administered include humans, monkeys, mice, rats, rabbits, dogs, cats, cows, horses, pigs, and sheep.

EXAMPLES

The present invention is explained in detail below with reference to Examples; however, the scope of the present invention is not limited to these Examples.

In the Examples, commercially available reagents were used, unless otherwise specified. Purif-Pack® SI, produced by Moritex Corp. (produced by Shoko Scientific Co., Ltd.); KP-Sil® Silica prepacked column, produced by Biotage; or HP-Sil® Silica prepacked column, produced by Biotage was used as the silica gel column chromatography. Purif-Pack® NH, produced by Moritex Corp (produced by Shoko Scientific Co., Ltd.); or KP-NH® prepacked column, produced by Biotage was used as the basic silica gel column chromatography. Kieselgel TM 60F 254, Art. 5744 produced by Merck, or $NH_2$ Silica Gel 60F254 Plate, produced by Wako, was used as the preparative thin-layer chromatography. NMR spectrum was measured by using AL400 (400 MHz; produced by JEOL), Mercury 400 (400 MHz; produced by Agilent Technologies, Inc.) spectrometer, or Inova 400 (400 MHz; produced by Agilent Technologies, Inc.) model spectrometer equipped with an OMNMR probe (produced by Protasis). When its deuterated solvent contains tetramethylsilane, the tetramethylsilane was used as the internal reference; and when tetramethylsilane is not contained, an NMR solvent was used as the reference. All of the delta values are shown by ppm. The microwave reaction was performed using Discover S-class, produced by CEM Corporation.

The LCMS spectrum was measured using an Acquity SQD (quadrupole), produced by Waters Corporation, under the following conditions.
Column: YMC-Triart C18, 2.0×50 mm, 1.9 μm (produced by YMC)
MS detection: ESI positive
UV detection: 254 and 210 nm
Column flow rate: 0.5 mL/min
Mobile phase: Water/acetonitrile (0.1% formic acid)
Injection volume: 1 μL

TABLE 1

| | Gradient | |
|---|---|---|
| Time (min) | Water | Acetonitrile |
| 0 | 95 | 5 |
| 0.1 | 95 | 5 |
| 2.1 | 5 | 95 |
| 3.0 | STOP. | |

Reversed-phase HPLC purification was performed using a preparative separation system available from Waters Corporation.
Column: Connected YMC-Actus Triart C18, 20×50 mm, 5 μm (produced by YMC) and YMC-Actus Triart C18, 20×10 mm, 5 μm (produced by YMC).
UV detection: 254 nm
MS detection: ESI positive
Column flow rate: 25 mL/min
Mobile phase: Water/acetonitrile (0.1% formic acid)
Injection volume: 0.1 to 0.5 mL
   Each symbol stands for the following.
s: Singlet
d: Doublet
t: Triplet
dd: Double Doublet
m: Multiplet
brs: Broad Singlet
DMSO-$d_6$: Deuterated dimethyl sulfoxide
$CDCl_3$: Deuterated chloroform
$CD_3OD$: Deuterated methanol
THF: Tetrahydrofuran DMF: N,N-dimethylformamide
DME: 1,2-Dimethoxyethane
HATU: O-(7-azabenzotriazol-1-yl)-N,N,N',N'-tetramethyluronium hexafluorophosphate

Example 1

(R)-N-(4-amino-5-(quinolin-3-yl)-6,7,8,9-tetrahydropyrimido[5,4-b]indolizin-8-yl)acrylamide (Compound I-1) and (S)-N-(4-amino-5-(quinolin-3-yl)-6,7,8,9-tetrahydropyrimido[5,4-b]indolizin-8-yl)acrylamide (Compound I-2)

[Chem. 9]

Compound I-1

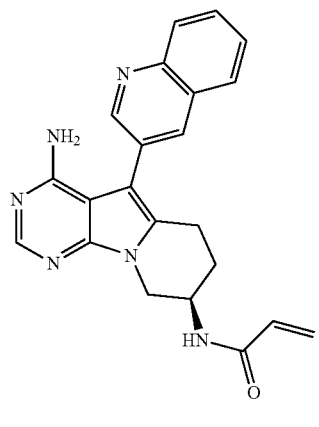

Compound I-2

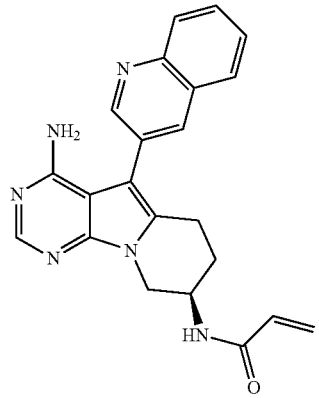

Step 1

Synthesis of 4-chloro-5-iodo-7H-pyrrolo[2,3-d]pyrimidine

[Chem. 10]

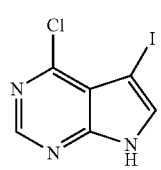

N-Iodosuccinimide (11.6 g) was added to a solution of 4-chloro-7H-pyrrolo[2,3-d]pyrimidine (7.52 g) in DMF (49 ml) at room temperature. The mixture was stirred at the same temperature for 1 hour, and water (150 ml) was added to the reaction mixture. The resulting precipitate was collected by filtration, washed with water, and dried to obtain the title compound as a light-yellow solid (13.57 g).

ESI-MS m/z 280, 282 (MH+).

Step 2

Synthesis of 1-bromo-2-(tert-butyldimethylsilyloxy)-3-butene

[Chem. 11]

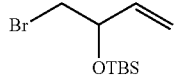

Imidazole (2.25 g) and tert-butyldimethylsilylchloride (4.75 g) were added to a solution of 1-bromo-3-buten-2-ol (4.5 g) in DMF (30 ml) at room temperature. The mixture was stirred at the same temperature for 16 hours, and water was added thereto, followed by extraction with hexane. The organic layer was washed with water, and dried over anhydrous sodium sulfate. The solvent was distilled off under reduced pressure to obtain the title compound as a light-yellow, oily substance (7.0 g).

Step 3

Synthesis of 7-(2-(tert-butyldimethylsilyloxy)-3-butenyl)-4-chloro-5-iodo-7H-pyrrolo[2,3-d]pyrimidine

[Chem. 12]

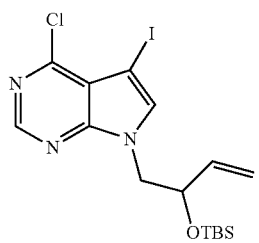

Potassium carbonate (2.2 g) was added to a solution of 4-chloro-5-iodo-7H-pyrrolo[2,3-d]pyrimidine (3.7 g) obtained in Step 1 and 1-bromo-2-(tert-butyldimethylsilyloxy)-3-butene (3.5 g) obtained in Step 2 in DMF (26 ml) at room temperature, and the mixture was stirred at 80° C. for 5 hours. After cooling the reaction mixture, water and ethyl acetate were added thereto, and the generated insoluble matter was filtered off. The organic layer was separated, washed with water and a saturated sodium chloride solution, and dried over anhydrous sodium sulfate. The solvent was then distilled off under reduced pressure. The resulting residue was purified by silica gel column chromatography (developing solvent: hexane/ethyl acetate) to obtain the title compound as a light-yellow solid (2.25 g).

ESI-MS m/z 464, 466 (MH+).

Step 4

Synthesis of 7-(2-(tert-butyldimethylsilyloxy)-3-butenyl)-5-iodo-7H-pyrrolo[2,3-d]pyrimidin-4-amine

[Chem. 13]

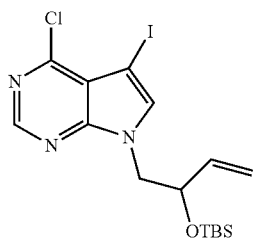

25% aqueous ammonia (9 ml) was added to a solution of 7-(2-(tert-butyldimethylsilyloxy)-3-butenyl)-4-chloro-5-iodo-7H-pyrrolo[2,3-d]pyrimidine (1.12 g) obtained in Step 3 in THF (7 ml). The mixture was stirred at 120° C. for 5 hours using a microwave reactor. The reaction mixture was cooled, and then diluted with water. The resulting precipitate was collected by filtration, washed with water, and then dried to obtain the title compound as a white solid (1.06 g).

ESI-MS m/z 445 (MH$^+$).

Step 5

Synthesis of 7-(2-(tert-butyldimethylsilyloxy)-3-butenyl)-5-(quinolin-3-yl)-7H-pyrrolo[2,3-d]pyrimidin-4-amine

[Chem. 14]

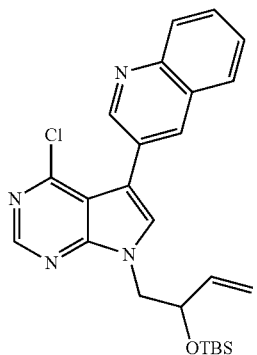

A mixture of 7-(2-(tert-butyldimethylsilyloxy)-3-butenyl)-5-iodo-7H-pyrrolo[2,3-d]pyrimidin-4-amine (3.62 g) obtained in Step 4, 3-quinolineboronic acid (1.47 g), sodium carbonate (1.72 g), 2-dicyclohexylphosphino-2',4',6'-triisopropylbiphenyl (154 mg), tris(dibenzylideneacetone)dipalladium (0) (148 mg), DME (40 ml), and water (16 ml) was stirred under a nitrogen atmosphere at 100° C. for 3 hours. After cooling, the reaction mixture was poured into water, followed by extraction with ethyl acetate. The organic layer was dried over anhydrous sodium sulfate, and the solvent was then distilled off under reduced pressure. The resulting residue was purified by silica gel column chromatography (developing solvent: hexane/ethyl acetate) to obtain the title compound as a light-yellow solid (2.13 g). ESI-MS m/z 446 (MH$^+$).

Step 6

Synthesis of 6-bromo-7-(2-(tert-butyldimethylsilyloxy)-3-butenyl)-5-(quinolin-3-yl)-7H-pyrrolo[2,3-d]pyrimidin-4-amine

[Chem. 15]

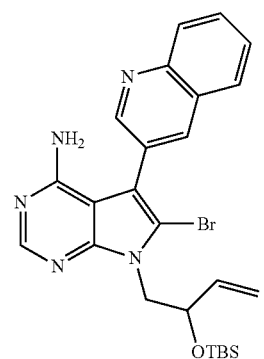

N-Bromosuccinimide (894 mg) was added to a solution of 7-(2-(tert-butyldimethylsilyloxy)-3-butenyl)-5-(quinolin-3-yl)-7H-pyrrolo[2,3-d]pyrimidin-4-amine (2.13 g) obtained in Step 5 in DMF (25 ml) at room temperature. After stirring at the same temperature for 30 minutes, the mixture was poured into a saturated aqueous sodium bicarbonate solution, followed by extraction with ethyl acetate. The organic layer was washed with water and a saturated sodium chloride solution, and dried over anhydrous sodium sulfate. The solvent was then distilled off under reduced pressure. The resulting residue was purified by silica gel column chromatography (developing solvent: hexane/ethyl acetate) to obtain the title compound as a yellow solid (2.26 g).

ESI-MS m/z 524, 526 (MH$^+$).

Step 7

Synthesis of 8-(tert-butyldimethylsilyloxy)-5-(quinolin-3-yl)-6,7,8,9-tetrahydropyrimido[5,4-b]indolizin-4-amine

[Chem. 16]

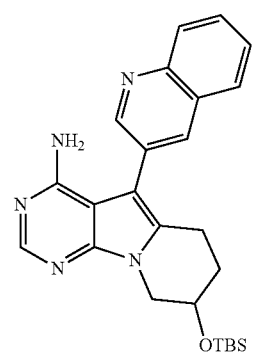

A solution of 0.5 M 9-borabicyclo[3.3.1]nonane in THF (50 ml) was added to a solution of 6-bromo-7-(2-(tert-butyldimethylsilyloxy)-3-butenyl)-5-(quinolin-3-yl)-7H-pyrrolo[2,3-d]pyrimidin-4-amine (2.26 g) obtained in Step 6 in THF (30 ml) under ice-cooling. The mixture was stirred at room temperature for 4 hours. After slowly adding a 3 N aqueous sodium hydroxide solution (19.5 ml) to the reaction mixture at room temperature, a [1,1'-bis(diphenylphosphino)ferrocene]dichloropalladium (II) complex with dichloromethane (676 mg) was added to the reaction mixture. The mixture was stirred under a nitrogen atmosphere at 70° C. for 4 hours. After cooling, the reaction mixture was poured into water, followed by extraction with ethyl acetate. The organic layer was dried over anhydrous sodium sulfate, and the solvent was distilled off under reduced pressure. The resulting residue was purified by silica gel column chromatography (developing solvent: hexane/ethyl acetate) to obtain the title compound as a yellow, oily substance (778 mg).

ESI-MS m/z 446 (MH⁺).

Step 8

Synthesis of 4-amino-5-(quinolin-3-yl)-6,7,8,9-tetrahydropyrimido[5,4-b]indolizin-8-ol

[Chem. 17]

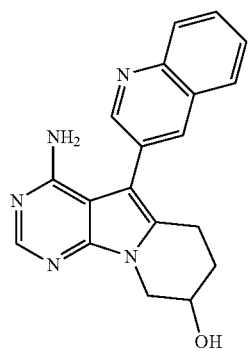

A solution of 1 M tetrabutylammonium fluoride in THF (2.09 ml) was added to a solution of 8-(tert-butyldimethylsilyloxy)-5-(quinolin-3-yl)-6,7,8,9-tetrahydropyrimido[5,4-b]indolizin-4-amine (778 mg) obtained in Step 7 in THF (20 ml) at room temperature. The mixture was stirred at the same temperature for 1 hour, and the solvent was distilled off under reduced pressure. The resulting residue was treated with a saturated aqueous ammonium chloride solution, followed by extraction with ethyl acetate. The organic layer was dried over anhydrous sodium sulfate, and the solvent was then distilled off under reduced pressure. The resulting residue was purified by silica gel column chromatography (developing solvent: chloroform/methanol) to obtain the title compound as a light-yellow solid (580 mg).

ESI-MS m/z 332 (MH⁺).

Step 9

Synthesis of 4-amino-5-(quinolin-3-yl)-6,7,8,9-tetrahydropyrimido[5,4-b]indolizin-8-yl methanesulfonate

[Chem. 18]

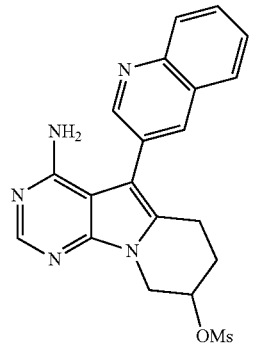

Triethylamine (0.157 ml) and methanesulfonyl chloride (0.074 ml) were added to a solution of 4-amino-5-(quinolin-3-yl)-6,7,8,9-tetrahydropyrimido[5,4-b]indolizin-8-ol (288 mg) obtained in Step 8 in THF (5 ml) under ice-cooling. After stirring at the same temperature for 15 minutes, the mixture was poured into a saturated aqueous sodium bicarbonate solution, followed by extraction with ethyl acetate. The organic layer was dried over anhydrous sodium sulfate. The solvent was distilled off under reduced pressure to obtain the title compound as a light-brown solid (615 mg).

ESI-MS m/z 410 (MH⁺).

Step 10

Synthesis of 8-azido-5-(quinolin-3-yl)-6,7,8,9-tetrahydropyrimido[5,4-b]indolizin-4-amine

[Chem. 19]

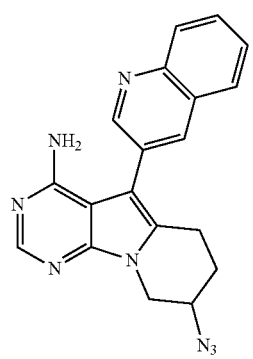

Sodium azide (361 mg) was added to a solution of 4-amino-5-(quinolin-3-yl)-6,7,8,9-tetrahydropyrimido[5,4-b]indolizin-8-yl methanesulfonate (758 mg) obtained in Step 9 in DMF (9 ml) at room temperature, and the mixture was stirred at 80° C. for 4 hours. After cooling, the reaction mixture was poured into water, followed by extraction with ethyl acetate. The organic layer was washed with water and a saturated sodium chloride solution, and dried over anhydrous sodium sulfate. The solvent was distilled off under reduced pressure to obtain the title compound as a yellow solid (508 mg).

ESI-MS m/z 357 (MH⁺).

Step 11

Synthesis of 5-(quinolin-3-yl)-6,7,8,9-tetrahydropyrimido[5,4-b]indolizine-4,8-diamine

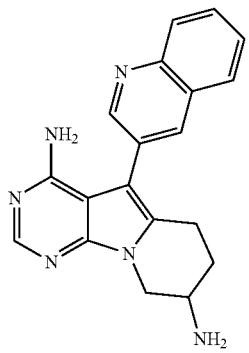

[Chem. 20]

Polymer-supported triphenylphosphine (~3.0 mmol/g, 1.42 g) was added to a solution of 8-azido-5-(quinolin-3-yl)-6,7,8,9-tetrahydropyrimido[5,4-b]indolizin-4-amine (508 mg) obtained in Step 10 in THF (10 ml) and water (1 ml) at room temperature. The reaction mixture was heated under reflux for 1 hour. After cooling, the reaction mixture was filtered through Celite, washed with ethanol, and the solvent was distilled off under reduced pressure. The resulting residue was purified by silica gel column chromatography (developing solvent: chloroform/methanol) to obtain the title compound as a yellow solid (342 mg). ESI-MS m/z 331 (MH$^+$).

Step 12

Synthesis of N-(4-amino-5-(quinolin-3-yl)-6,7,8,9-tetrahydropyrimido[5,4-b]indolizin-8-yl)acrylamide

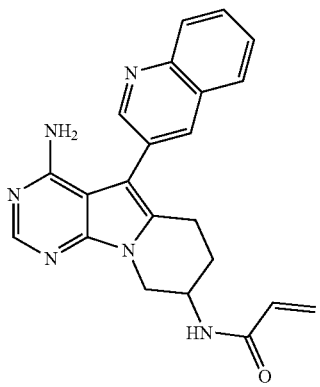

[Chem. 21]

N,N-diisopropylethylamine (0.033 ml) and acryloyl chloride (0.0154 ml) were added to a solution of 5-(quinolin-3-yl)-6,7,8,9-tetrahydropyrimido[5,4-b]indolizine-4,8-diamine (68 mg) obtained in Step 11 in chloroform (2.5 ml) under ice-cooling. After stirring at the same temperature for 15 minutes, the mixture was poured into a saturated aqueous sodium bicarbonate solution, followed by extraction with chloroform. The organic layer was dried over anhydrous sodium sulfate, and the solvent was then distilled off under reduced pressure. The resulting residue was purified by silica gel column chromatography (developing solvent: chloroform/methanol) to obtain the title compound as a yellow solid (35.4 mg).

$^1$H-NMR (CDCl$_3$) δ: 2.14 (2H, d, J=5.6 Hz), 3.04 (2H, t, J=6.2 Hz), 4.17 (1H, dd, J=12.7, 5.8 Hz), 4.46 (1H, dd, J=12.7, 4.5 Hz), 4.70-4.80 (1H, m), 4.89 (2H, brs), 5.71 (1H, d, J=10.2 Hz), 6.21 (1H, dd, J=16.8, 10.2 Hz), 6.39 (1H, d, J=16.8 Hz), 6.50 (1H, d, J=7.0 Hz), 7.62 (1H, t, J=7.4 Hz), 7.77 (1H, t, J=7.4 Hz), 7.87 (1H, d, J=8.0 Hz), 8.15 (1H, d, J=8.0 Hz), 8.25 (1H, s), 8.32 (1H, s), 9.00 (1H, s). ESI-MS m/z 385 (MH$^+$).

Step 13

Separation of N-(4-amino-5-(quinolin-3-yl)-6,7,8,9-tetrahydropyrimido[5,4-b]indolizin-8-yl)acrylamide enantiomer A and N-(4-amino-5-(quinolin-3-yl)-6,7,8,9-tetrahydropyrimido[5,4-b]indolizin-8-yl)acrylamide enantiomer B

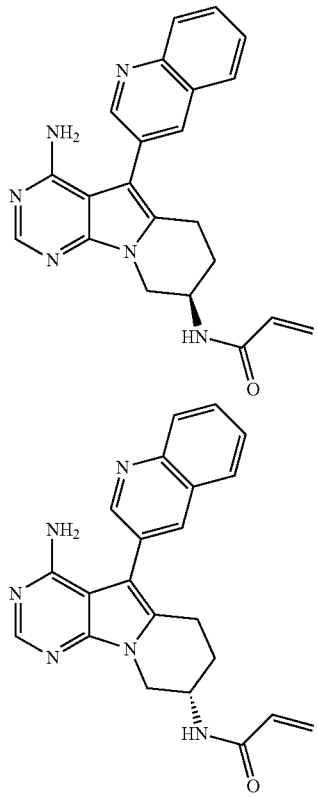

[Chem. 22]

N-(4-amino-5-(quinolin-3-yl)-6,7,8,9-tetrahydropyrimido[5,4-b]indolizin-8-yl)acrylamide (197 mg) obtained in Step 12 was subjected to optical resolution using a column for optical resolution (CHIRALPAK AD-H 20 mm×250 mm, manufactured by Daicel Chemical Industries, Ltd.), mobile phase: hexane/ethanol/triethylamine, 50:50:0.1, flow rate: 10 ml/min) to obtain 72.4 mg of enantiomer A (retention time: 15.4 min, (R)-N-(4-amino-5-(quinolin-3-yl)-6,7,8,9-tetrahydropyrimido[5,4-b]indolizin-8-yl)acrylamide (Compound I-1)) and 78.3 mg of enantiomer B (retention time: 32.5 min, (S)-N-(4-amino-5-(quinolin-3-yl)-6,7,8,9-tetrahydropyrimido[5,4-b]indolizin-8-yl)acrylamide (Compound I-2)) as a light-yellow solid.

Enantiomer A
ESI-MS m/z 385 (MH$^+$).

Enantiomer B
ESI-MS m/z 385 (MH$^+$).

When the (R)-N-(4-amino-5-(quinolin-3-yl)-6,7,8,9-tetrahydropyrimido[5,4-b]indolizin-8-yl)acrylamide obtained in the same method as Example 2 described later was subjected to a column treatment under the same conditions as described above, its retention time was the same as that of enantiomer A. It was confirmed that the enantiomer A was an R isomer, i.e., Compound I-1; and that the enantiomer B was an S isomer, i.e., Compound I-2.

Example 2

(R)-N-(4-amino-5-(quinolin-3-yl)-6,7,8,9-tetrahydropyrimido[5,4-b]indolizin-8-yl)acrylamide (Compound I-1)

Step 1

Synthesis of (S)-2-(tert-butyldimethylsilyloxy)-3-butenyl 4-methylbenzenesulfonate

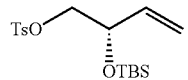

[Chem. 23]

In accordance with Step 2 of Example 1, except that (S)-3-butene-1,2-diol-1-(p-toluenesulfonate) was used in place of 1-bromo-3-buten-2-ol, the title compound was obtained as a colorless, oily substance (2.74 g).

Step 2

Synthesis of (R)-N-(4-amino-5-(quinolin-3-yl)-6,7,8,9-tetrahydropyrimido[5,4-b]indolizin-8-yl)acrylamide

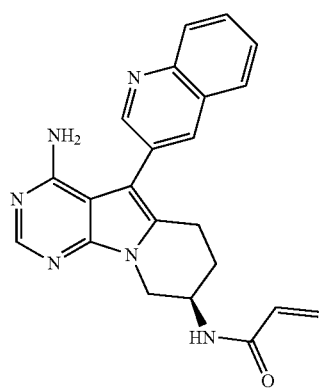

[Chem. 24]

In accordance with Steps 1 to 12 of Example 1, except that (S)-2-(tert-butyldimethylsilyloxy)-3-butenyl 4-methylbenzenesulfonate obtained in Step 1 was used in place of 1-bromo-2-(tert-butyldimethylsilyloxy)-3-buten, the title compound was obtained as a yellow solid (13.9 mg).

Example 3

N-(4-amino-5-(quinolin-3-yl)-6,7,8,9-tetrahydropyrimido[5,4-b]indolizin-8-yl)-N-methylacrylamide (Compound I-3)

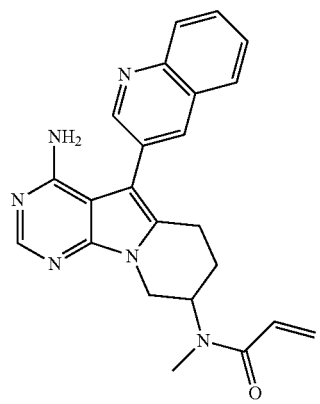

[Chem. 25]

Step 1

Synthesis of N$^8$-methyl-5-(quinolin-3-yl)-6,7,8,9-tetrahydropyrimido[5,4-b]indolizine-4,8-diamine

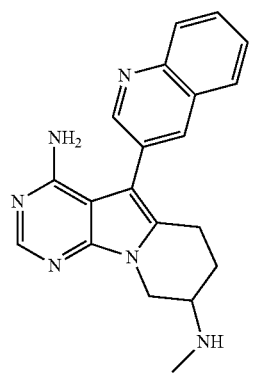

[Chem. 26]

4-Amino-5-(quinolin-3-yl)-6,7,8,9-tetrahydropyrimido[5,4-b]indolizin-8-yl methanesulfonate (30 mg) obtained in Step 9 of Example 1 was dissolved in a solution of methylamine in 40% methanol (1 ml). The solution was stirred at 60° C. for 1 hour and at 80° C. for 22 hours. After cooling, the reaction mixture was concentrated under reduced pressure. The resulting residue was purified by silica gel column chromatography (developing solvent: ethyl acetate/methanol) to obtain the title compound as a light-yellow, oily substance (8.1 mg).

ESI-MS m/z 345 (MH$^+$).

Step 2

Synthesis of N-(4-amino-5-(quinolin-3-yl)-6,7,8,9-tetrahydropyrimido[5,4-b]indolizin-8-yl)-N-methylacrylamide

[Chem. 27]

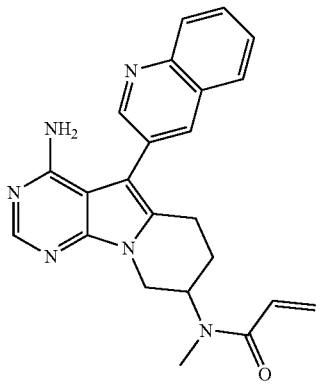

In accordance with Step 12 of Example 1, except that N⁸-methyl-5-(quinolin-3-yl)-6,7,8,9-tetrahydropyrimido[5,4-b]indolizine-4,8-diamine obtained in Step 1 was used in place of 5-(quinolin-3-yl)-6,7,8,9-tetrahydropyrimido[5,4-b]indolizine-4,8-diamine used in Step 12 of Example 1, the title compound was obtained as a light-yellow solid (6.2 mg).

$^1$H-NMR (CDCl$_3$) δ: 1.90-2.15 (2H, m), 3.00-3.15 (2H, m), 3.06 (3H, s), 3.90-4.03 (1H, m), 4.56-4.64 (1H, m), 5.06 (2H, brs), 5.15-5.30 (1H, m), 5.77 (1H, d, J=10.2 Hz), 6.38 (1H, d, J=16.6 Hz), 6.54-6.70 (1H, m), 7.63 (1H, t, J=7.3 Hz), 7.78 (1H, t, J=7.3 Hz), 7.88 (1H, d, J=8.0 Hz), 8.16 (1H, s), 8.17 (1H, d, J=8.0 Hz), 8.31 (1H, s), 9.01 (1H, s).

ESI-MS m/z 399 (MH⁺).

Example 4

(E)-N-(4-amino-5-(quinolin-3-yl)-6,7,8,9-tetrahydropyrimido[5,4-b]indolizin-8-yl)-4-(dimethylamino)-2-butenamide (Compound I-4)

[Chem. 28]

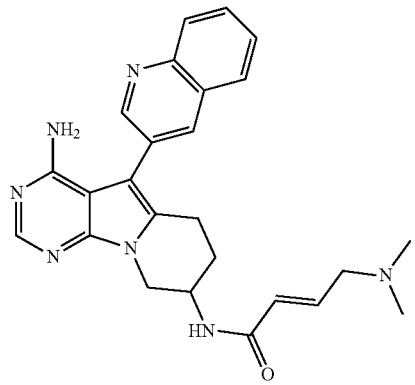

HATU (10.3 mg) and 5-(quinolin-3-yl)-6,7,8,9-tetrahydropyrimido[5,4-b]indolizine-4,8-diamine (8.8 mg) obtained in Step 11 of Example 1 were added to a solution of trans-4-dimethylaminocrotonic acid hydrochloride (4.5 mg) in DMF (0.5 ml) at room temperature. After being stirred for 1 hour at the same temperature, the mixture was poured into a saturated aqueous sodium bicarbonate solution, followed by extraction with ethyl acetate. The organic layer was dried over anhydrous sodium sulfate, and the solvent was then distilled off under reduced pressure. The resulting residue was purified by preparative thin-layer chromatography (produced by Wako, NH$_2$ silica-gel 60 F254 plate, developing solvent: chloroform/methanol) to obtain the title compound as a light-yellow solid (6.4 mg).

$^1$H-NMR (CDCl$_2$) δ: 2.05-2.20 (2H, m), 2.27 (6H, s), 2.49-2.65 (4H, m), 4.10-4.20 (1H, m), 4.46-5.02 (1H, m), 4.68-4.77 (1H, m), 4.91 (2H, brs), 6.06 (1H, d, J=15.4 Hz), 6.39 (1H, d, J=7.0 Hz), 6.85-6.95 (1H, m), 7.62 (1H, t, J=7.4 Hz), 7.77 (1H, t, J=7.4 Hz), 7.87 (1H, d, J=8.0 Hz), 8.15 (1H, d, J=8.0 Hz), 8.17 (1H, s), 8.25 (1H, s), 9.00 (1H, s). ESI-MS m/z 442 (MH⁺).

Example 5

(S,E)-N-(4-amino-5-(quinolin-3-yl)-6,7,8,9-tetrahydropyrimido[5,4-b]indolizin-8-yl)-3-chloroacrylamide (Compound I-5)

[Chem. 29]

Trans-3-chloroacrylic acid (399.5 mg) was added to a suspension of 5-(quinolin-3-yl)-6,7,8,9-tetrahydropyrimido[5,4-b]indolizine-4,8-diamine (498.0 mg) obtained in Step 11 of Example 1 in DMF (8 ml) at room temperature. After dissolving, 1-(3-dimethylaminopropyl)-3-ethylcarbodiimide hydrochloride (350.1 mg) was added thereto under ice-cooling, and the mixture was stirred for 1 hour at the same temperature. The reaction mixture was poured into a saturated aqueous sodium bicarbonate solution, followed by extraction with ethyl acetate. The organic layer was dried over anhydrous sodium sulfate, and the solvent was then distilled off under reduced pressure. The resulting residue was purified by silica gel column chromatography (developing solvent: ethyl acetate/methanol) to obtain the title compound as a light-yellow solid (261.2 mg).

$^1$H-NMR (DMSO-d$_6$) δ: 1.84-2.07 (2H, m), 2.92-3.08 (2H, m), 3.88-4.02 (1H, m), 4.27-4.43 (2H, m), 6.07 (2H, brs), 6.48 (1H, d, J=13.4 Hz), 7.31 (1H, d, J=13.2 Hz), 7.63 (1H, t, J=7.4 Hz), 7.75 (1H, t, J=7.6 Hz), 8.03 (1H, d, J=10.7 Hz), 8.05 (1H, d, J=10.7 Hz), 8.13 (1H, s), 8.29 (1H, d, J=2.0 Hz), 8.53 (1H, d, J=6.6 Hz), 8.92 (1H, d, J=2.2 Hz).

ESI-MS m/z 419, 421 (MH⁺).

Example 6

(S,Z)—N-(4-amino-5-(quinolin-3-yl)-6,7,8,9-tetrahydropyrimido[5,4-b]indolizin-8-yl)-3-chloroacrylamide (Compound I-6)

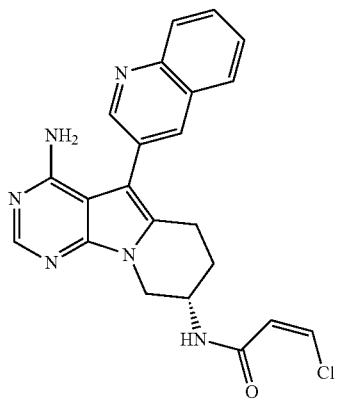

[Chem. 30]

In accordance with Example 5, except that cis-3-chloroacrylic acid was used in place of trans-3-chloroacrylic acid used in Example 5, the title compound was obtained as a light-yellow solid (93 mg).

¹H-NMR (DMSO-d₆) δ: 1.82-1.96 (1H, m), 1.96-2.07 (1H, m), 2.92-3.08 (2H, m), 3.85-3.97 (1H, m), 4.27-4.41 (2H, m), 6.05 (2H, brs), 6.39 (1H, d, J=8.0 Hz), 6.77 (1H, d, J=8.0 Hz), 7.63 (1H, t, J=7.4 Hz), 7.75 (1H, t, J=7.4 Hz), 8.02 (1H, d, J=11.4 Hz), 8.04 (1H, d, J=11.4 Hz), 8.13 (1H, s), 8.29 (1H, d, J=2.0 Hz), 8.50 (1H, d, J=6.3 Hz), 8.92 (1H, d, J=2.0 Hz).

ESI-MS m/z 419, 421 (MH⁺).

Example 7

(S)-N-(4-amino-5-(quinolin-3-yl)-7,8,9,10-tetrahydro-6H-pyrimido[5',4':4,5]pyrrolo[1,2-a]azepin-8-yl)acrylamide (Compound I-7)

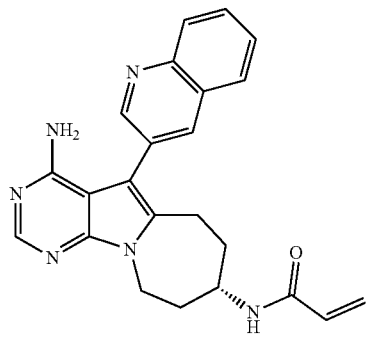

[Chem. 31]

Step 1

Synthesis of (R)-tert-butyl (1-hydroxy-5-(methylthio)pentan-3-yl)carbamate

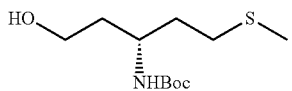

[Chem. 32]

N-methylmorpholine (3.63 ml) and ethyl chloroformate (3.01 ml) were added to a solution of (R)-3-((tert-butoxycarbonyl)amino)-5-(methylthio)pentanoic acid (7.92 g) in THF (79.2 ml) at −10° C. After stirring at −10° C. for 15 minutes, the generated insoluble matter was filtered off. An aqueous solution of sodium borohydride (1.55 g) (15 ml) was added to the filtrate at −10° C., and the mixture was stirred at −10° C. for 1 hour. A saturated aqueous ammonium chloride solution was added thereto, and the mixture was stirred at room temperature for 30 minutes. Ethyl acetate was added thereto to separate the organic layer. The organic layer was washed with a 0.5 N aqueous potassium hydrogensulfate solution, water, a 0.5 N aqueous sodium hydroxide solution and a saturated sodium chloride solution, and dried over anhydrous sodium sulfate. The solvent was then distilled off under reduced pressure. The resulting residue was purified by silica gel column chromatography (developing solvent: chloroform/ethyl acetate) to obtain the title compound as a light-yellow, oily substance (7.18 g).

Step 2

Synthesis of tert-butyl ((3R)-1-hydroxy-5-(methylsulfinyl)pentan-3-yl)carbamate

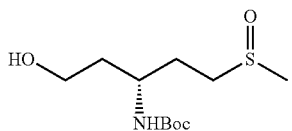

[Chem. 33]

A suspension of sodium periodate (7.0 g) in water (32 ml) was added to a solution of (R)-tert-butyl (1-hydroxy-5-(methylthio)pentan-3-yl)carbamate (8.16 g) obtained in Step 1 in methanol (98 ml) at a temperature 10° C. or lower, and the mixture was stirred at room temperature for 2 hours. The generated insoluble matter was filtered off, and the filtrate was distilled off under reduced pressure. The resulting residue was dissolved in a saturated sodium chloride solution, followed by extraction with chloroform for 3 times. The organic layer was dried over anhydrous sodium sulfate, and the solvent was distilled off under reduced pressure to obtain the title compound as a light-yellow solid (9.38 g).

Step 3

Synthesis of (R)-tert-butyl (5-hydroxypent-1-en-3-yl)carbamate

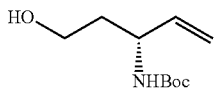

[Chem. 34]

Sodium acetate (13.45 g) was added to a solution of tert-butyl ((3R)-1-hydroxy-5-(methylsulfinyl)pentan-3-yl)carbamate (9.38 g) obtained in Step 2 in 1,2-dichlorobenzene (140 ml) at room temperature. The mixture was stirred at an internal temperature of 166° C. for 18 hours. After cooling the reaction mixture, the insoluble matter was filtered off, and 1,2-dichlorobenzene was distilled off under reduced pressure. The resulting residue was dissolved in ethyl acetate, washed with a saturated aqueous sodium chloride solution, water, and a saturated sodium chloride solution; and dried over anhydrous sodium sulfate. The solvent was then distilled off under reduced pressure. The resulting residue was purified by silica gel column chromatography (developing solvent: hexane/ethyl acetate) to obtain the title compound 2.50 g as a light-yellow, oily substance.

Step 4

Synthesis of (R)-tert-butyl (5-(4-chloro-5-iodo-7H-pyrrolo[2,3-d]pyrimidin-7-yl)pent-1-en-3-yl)carbamate

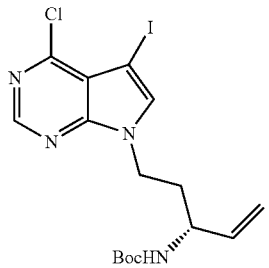

[Chem. 35]

Triphenylphosphine (3.25 g) was added to and dissolved in a solution of (R)-tert-butyl (5-hydroxypent-1-en-3-yl)carbamate (2.5 g) obtained in Step 3 and 4-chloro-5-iodo-7H-pyrrolo[2,3-d]pyrimidine (2.31 g) obtained in Step 1 of Example 1 in DME (23 ml) under ice-cooling. Thereafter, diisopropyl azodicarboxylate (2.44 ml) was gradually added thereto. The reaction mixture was stirred under ice-cooling for 30 minutes and at room temperature for 1 hour, and the solvent was then distilled off under reduced pressure. The resulting residue was dissolved in ethyl acetate, washed with water, and dried over anhydrous sodium sulfate. The solvent was then distilled off under reduced pressure. The resulting residue was purified by silica gel column chromatography (developing solvent: hexane/ethyl acetate) to obtain the title compound as a light-yellow solid (3.49 g).

ESI-MS m/z 463, 465 (MH$^+$).

Step 5

Synthesis of (R)-tert-butyl (5-(4-amino-5-iodo-7H-pyrrolo[2,3-d]pyrimidin-7-yl)pent-1-en-3-yl)carbamate

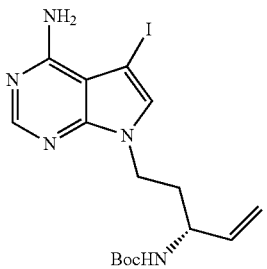

[Chem. 36]

28% aqueous ammonia (17.5 ml) was added to a solution of (R)-tert-butyl (5-(4-chloro-5-iodo-7H-pyrrolo[2,3-d]pyrimidine-7-yl)pent-1-en-3-yl)carbamate (3.49 g) obtained in Step 4 in DME (17.5 ml), and the mixture was stirred in an autoclave at an internal temperature of 105° C. for 8 hours. After cooling the reaction mixture, water (70 ml) was added thereto, and the mixture was stirred at room temperature for 4 hours. The resulting precipitate was collected by filtration, washed with water, and dried to obtain the title compound as a light-yellow solid (3.20 g).

ESI-MS m/z 444 (MH$^+$).

Step 6

Synthesis of (R)-tert-butyl (5-(4-amino-5-(quinolin-3-yl)-7H-pyrrolo[2,3-d]pyrimidin-7-yl)pent-1-en-3-yl)carbamate

[Chem. 37]

A mixture of (R)-tert-butyl (5-(4-amino-5-iodo-7H-pyrrolo[2,3-d]pyrimidin-7-yl)pent-1-en-3-yl)carbamate (3.2 g) obtained in Step 5, 3-quinolineboronic acid (1.37 g), sodium carbonate (843 mg), tetrakis(triphenylphosphine)palladium (250 mg), DME (32 ml) and water (32 ml) was stirred under a nitrogen atmosphere at 100° C. for 6 hours. After cooling the reaction mixture, a saturated aqueous sodium bicarbonate solution and ethyl acetate were added thereto. The resulting mixture was stirred at room temperature for 30 minutes. After filtering off the insoluble matter, the organic layer was separated and dried over anhydrous sodium sulfate. The solvent was then distilled off under reduced pressure. The resulting residue was purified by silica gel column chromatography (developing solvent: hexane/ethyl acetate, ethyl acetate/methanol) to obtain the title compound as a light-orange solid (3.21 g).

ESI-MS m/z 445 (MH$^+$).

Step 7

Synthesis of (R)-tert-butyl (5-(4-amino-6-bromo-5-(quinolin-3-yl)-7H-pyrrolo[2,3-d]pyrimidin-7-yl)pent-1-en-3-yl)carbamate

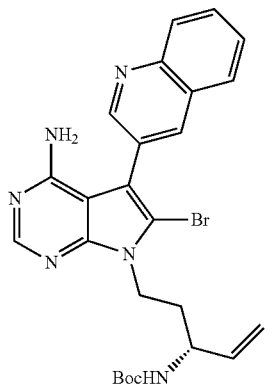

[Chem. 38]

A solution of N-bromosuccinimide (1.35 g) in THF (23 ml) was added to a solution of (R)-tert-butyl (5-(4-amino-5-(quinolin-3-yl)-7H-pyrrolo[2,3-d]pyrimidin-7-yl)pent-1-en-3-yl)carbamate (3.21 g) obtained in Step 6 in THF (26 ml) under ice-cooling over 30 minutes. The mixture was stirred under ice-cooling for 30 minutes. After adding a 5% aqueous sodium thiosulfate solution, the mixture was poured into a saturated aqueous sodium bicarbonate solution, followed by extraction with ethyl acetate. The organic layer was washed with a saturated sodium chloride solution and dried over anhydrous sodium sulfate. The solvent was then distilled off under reduced pressure. The resulting residue was purified by silica gel column chromatography (developing solvent: hexane/ethyl acetate, ethyl acetate/methanol) to obtain the title compound as a light-brown solid (3.15 g).

ESI-MS m/z 523, 525 (MH$^+$).

Step 8

Synthesis of (S)-tert-butyl (4-amino-5-(quinolin-3-yl)-7,8,9,10-tetrahydro-6H-pyrimido[5',4':4,5]pyrrolo[1,2-a]azepin-8-yl)carbamate

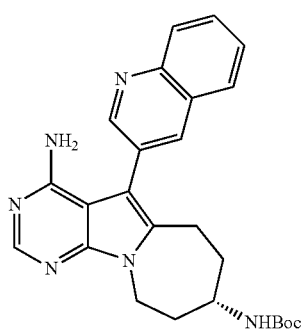

[Chem. 39]

(R)-tert-Butyl (5-(4-amino-6-bromo-5-(quinolin-3-yl)-7H-pyrrolo[2,3-d]pyrimidin-7-yl)pent-1-en-3-yl)carbamate (994 mg) obtained in Step 7 was added to a solution of 9-borabicyclo[3.3.1]nonane in 0.5 M THF (22.8 ml) at room temperature. The mixture was stirred at the same temperature for 1 hour, and a 4 N aqueous sodium hydroxide solution (5.7 ml) was carefully added thereto. After nitrogen purging, the mixture was heated to have an internal temperature of 55° C. Tetrakis(triphenylphosphine)palladium (275 mg) was added thereto, and the mixture was stirred at an internal temperature of 66° C. for 15 hours. After cooling the reaction mixture, the organic layer was separated, and toluene (7.7 ml) and a 20% aqueous ammonium chloride solution (5 ml) were added thereto. The organic layer was separated, washed with a 20% saline solution, and SH silica gel (produced by Fuji Silysia, 1 g) was added thereto. The mixture was stirred at an internal temperature 68° C. for 1 hour, and SH silica gel (produced by Fuji Silysia, 1 g) was added thereto. The mixture was stirred at an internal temperature of 68° C. for 1 hour. After cooling, the silica gel was filtered off, and the solvent was distilled off under reduced pressure. The resulting residue was purified by silica gel column chromatography (developing solvent: ethyl acetate/methanol) to obtain the title compound as a yellow solid (439 mg).

ESI-MS m/z 445 (MH$^+$).

Step 9

Synthesis of (S)-5-(quinolin-3-yl)-7,8,9,10-tetrahydro-6H-pyrimido[5',4':4,5]pyrrolo[1,2-a]azepin-4,8-diamine

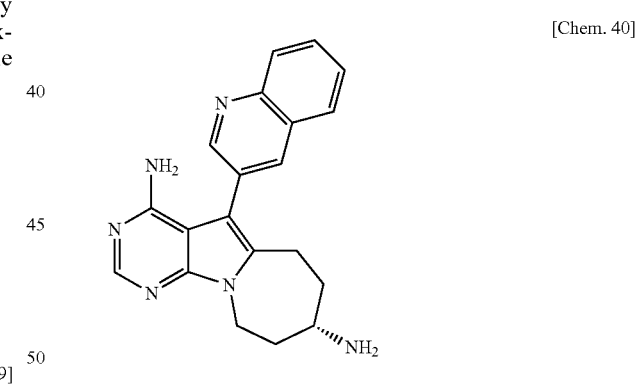

[Chem. 40]

5 N Hydrochloric acid (1 ml) was added to a solution of (S)-tert-butyl (4-amino-5-(quinolin-3-yl)-7,8,9,10-tetrahydro-6H-pyrimido[5',4':4,5]pyrrolo[1,2-a]azepin-8-yl)carbamate (436 mg) obtained in Step 8 in ethanol (4 ml) at room temperature. The mixture was stirred at 60° C. for 3 hours. After cooling, the reaction mixture was basified with a 5 N aqueous sodium hydroxide solution, followed by extraction with chloroform. The organic layer was dried over anhydrous sodium sulfate, and the solvent was distilled off under reduced pressure. The resulting residue was purified by silica gel column chromatography (developing solvent: chloroform/methanol) to obtain the title compound as a light-yellow solid (320 mg).

ESI-MS m/z 345 (MH$^+$).

Step 10

Synthesis of (S)-N-(4-amino-5-(quinolin-3-yl)-7,8,9,10-tetrahydro-6H-pyrimido[5',4':4,5]pyrrolo[1,2-a]azepin-8-yl)acrylamide

[Chem. 41]

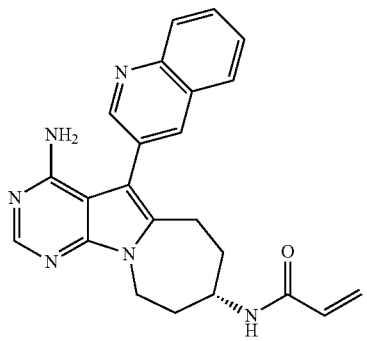

N,N-Diisopropylethylamine (0.192 ml) and a solution of acryloyl chloride (83.3 mg) in acetonitrile (0.83 ml) were added to an acetonitrile (1.6 ml)-water (1.6 ml) solution of the (S)-5-(quinolin-3-yl)-7,8,9,10-tetrahydro-6H-pyrimido[5',4':4,5]pyrrolo[1,2-a]azepin-4,8-diamine (317 mg) obtained in Step 9 under ice-cooling. After being stirred at the same temperature for 15 minutes, the mixture was poured into a saturated aqueous sodium bicarbonate solution, followed by extraction with chloroform. The organic layer was dried over anhydrous sodium sulfate, and the solvent was then distilled off under reduced pressure. The resulting residue was purified by silica gel column chromatography (developing solvent: ethyl acetate/methanol) to obtain the title compound as a light-yellow solid (226 mg).

$^1$H-NMR (DMSO-d$_6$) δ: 1.37-1.56 (2H, m), 1.98-2.20 (2H, m), 2.75-2.83 (1H, m), 2.88-2.97 (1H, m), 3.96-4.18 (2H, m), 4.78-4.90 (1H, m), 5.58 (1H, dd, J=10.0, 2.2 Hz), 5.93 (2H, brs), 6.19 (1H, dd, J=17.1, 2.2 Hz), 6.21 (1H, dd, J=17.1, 10.0 Hz), 7.64 (1H, t, J=7.4 Hz), 7.77 (1H, t, J=7.4 Hz), 8.01-8.09 (2H, m), 8.14 (1H, s), 8.17 (1H, d, J=7.6 Hz), 8.27 (1H, d, J=2.0 Hz), 8.85 (1H, d, J=2.0 Hz).

ESI-MS m/z 399 (MH$^+$).

Example 8

(S)-N-(4-amino-5-(quinolin-3-yl)-7,8,9,10-tetrahydro-6H-pyrimido[5',4':4,5]pyrrolo[1,2-a]azepin-9-yl)acrylamide

[Chem. 42]

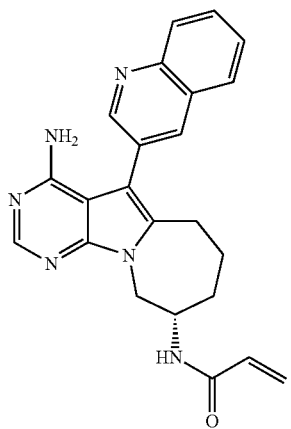

Step 1

Synthesis of (S)-tert-butyl (1-hydroxypent-4-en-2-yl)carbamate

[Chem. 43]

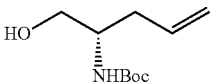

N-methylmorpholine (15.25 ml) and ethyl chloroformate (12.60 ml) were added to a solution of (S)-2-((tert-butoxycarbonyl)amino)pent-4-enoic acid (25.0 g) in THF (250 ml) at −15° C. After stirring the mixture at −15° C. for 15 minutes, the generated insoluble matter was filtered off. A solution of sodium borohydride (3.23 g) in water (32 ml) was added to the filtrate at −15° C., and the mixture was stirred at −15° C. for 1 hour. A saturated aqueous ammonium chloride solution was added thereto, and the mixture was stirred at room temperature for 30 minutes. Ethyl acetate was added thereto to separate the organic layer. The organic layer was washed with a 0.5 N aqueous potassium hydrogensulfate solution, water, a 0.5 N aqueous sodium hydroxide solution, and a saturated sodium chloride solution; and dried over anhydrous sodium sulfate. The solvent was then distilled off under reduced pressure. The resulting residue was purified by silica gel column chromatography (developing solvent: hexane/ethyl acetate) to obtain the title compound as a light-yellow, oily substance (11.93 g).

Step 2

Synthesis of (S)-N-(4-amino-5-(quinolin-3-yl)-7,8,9,10-tetrahydro-6H-pyrimido[5',4':4,5]pyrrolo[1,2-a]azepin-9-yl)acrylamide

[Chem. 44]

In accordance with Steps 4 to 10 of Example 7, except that (S)-tert-butyl (1-hydroxypent-4-en-2-yl)carbamate obtained in Step 1 was used in place of (R)-tert-butyl (5-hydroxypent-1-en-3-yl)carbamate obtained in Step 4 of Example 7, the title compound was obtained as a milky-white solid (400.0 mg).

$^1$H-NMR (DMSO-d$_6$) δ: 1.57-1.65 (1H, m), 1.78-1.86 (1H, m), 1.93-2.05 (2H, m), 2.77-2.89 (2H, m), 3.98-4.04 (1H, m), 4.21-4.26 (1H, m), 4.63 (1H, d, J=13.7 Hz), 5.60 (1H, dd, J=10.0, 2.4 Hz), 5.93 (1H, brs), 6.12 (1H, dd, J=17.1, 2.4 Hz), 6.25 (1H, dd, J=17.1, 10.0 Hz), 7.63-7.67 (1H, m), 7.77-7.81 (1H, m), 8.07 (1H, t, J=8.8 Hz), 8.12 (1H, s), 8.15 (1H, d, J=7.6 Hz), 8.28 (1H, d, J=2.2 Hz), 8.87 (1H, d, J=2.2 Hz).

ESI-MS m/z 399 (MH$^+$).

Example 9

(R)-N-(4-amino-5-(quinolin-3-yl)-7,8,9,10-tetrahydro-6H-pyrimido[5',4':4,5]pyrrolo[1,2-a]azepin-9-yl)acrylamide (Compound I-9)

[Chem. 45]

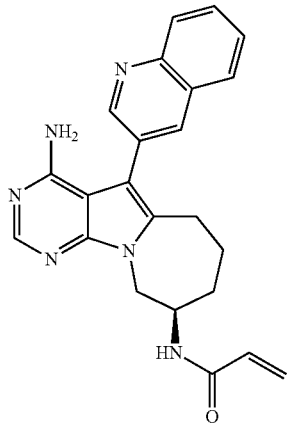

Step 1

Synthesis of (R)-tert-butyl (1-hydroxypent-4-en-2-yl)carbamate

[Chem. 46]

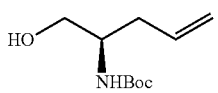

In accordance with Step 1 of Example 8, except that (R)-2-((tert-butoxycarbonyl)amino)pent-4-enoic acid was used in place of (S)-2-((tert-butoxycarbonyl)amino)pent-4-enoic acid used in Step 1 of Example 8, the title compound was obtained as a light-yellow, oily substance.

Step 2

Synthesis of (R)-N-(4-amino-5-(quinolin-3-yl)-7,8,9,10-tetrahydro-6H-pyrimido[5',4':4,5]pyrrolo[1,2-a]azepin-9-yl)acrylamide

[Chem. 47]

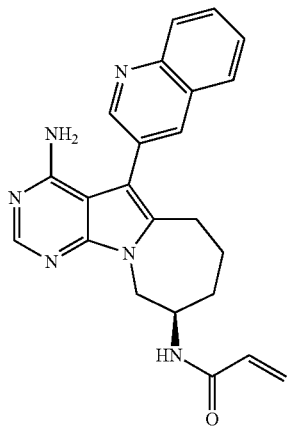

In accordance with Steps 4 to 10 of Example 7, except that (R)-tert-butyl (1-hydroxypent-4-en-2-yl)carbamate obtained in Step 1 was used in place of (R)-tert-butyl (5-hydroxypent-1-en-3-yl)carbamate used in Step 4 of Example 7, the title compound was obtained as a milky-white solid (115.5 mg).

$^1$H-NMR (DMSO-$d_6$) δ: 1.57-1.65 (1H, m), 1.78-1.86 (1H, m), 1.93-2.05 (2H, m), 2.77-2.89 (2H, m), 3.98-4.04 (1H, m), 4.21-4.26 (1H, m), 4.63 (1H, d, J=13.7 Hz), 5.60 (1H, dd, J=10.0, 2.4 Hz), 5.93 (1H, brs), 6.12 (1H, dd, J=17.1, 2.4 Hz), 6.25 (1H, dd, J=17.1, 10.0 Hz), 7.63-7.67 (1H, m), 7.77-7.81 (1H, m), 8.07 (1H, t, J=8.8 Hz), 8.12 (1H, s), 8.15 (1H, d, J=7.6 Hz), 8.28 (1H, d, J=2.2 Hz), 8.87 (1H, d, J=2.2 Hz).

ESI-MS m/z 399 (MH$^+$).

Comparative Example 1

Synthesis of N-(3-(4-amino-6,7,8,9-tetrahydropyrimido[5,4-b]indolizin-5-yl)phenyl)benzamide

[Chem. 48]

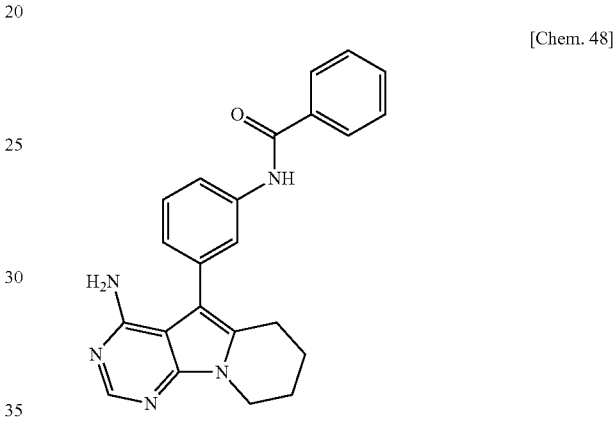

Synthesis was performed according to the method disclosed in WO2006/102079.

ESI-MS m/z 384 (MH$^+$).

The methods for synthesizing the production intermediates of the compounds of the present invention are explained below. The methods are not limited thereto.

Reference Example 1

(S)-tert-Butyl (1-(4-amino-6-bromo-5-(quinolin-3-yl)-7H-pyrrolo[2,3-d]pyrimidin-7-yl)but-3-en-2-yl)carbamate

[Chem. 49]

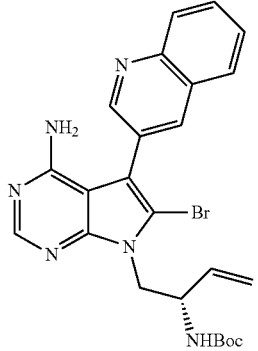

Step 1

Synthesis of (S)-tert-butyl (1-(4-chloro-5-iodo-7H-pyrrolo[2,3-d]pyrimidin-7-yl)but-3-en-2-yl)carbamate

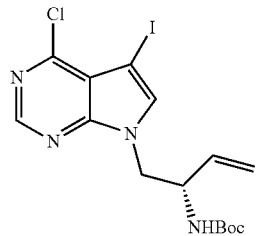

[Chem. 50]

Diisopropyl azodicarboxylate (2.44 ml) was slowly added to a solution of triphenylphosphine (13.1 g) in tetrahydrofuran (70 ml) under ice-cooling. The reaction mixture was stirred under ice-cooling for 1 hour, and then a solution of (S)-tert-butyl (1-hydroxybut-3-en-2-yl)carbamate (7.0 g) synthesized according to the method disclosed in Non-patent Literature Org. Lett., 2005, vol. 7, No. 5, pp. 847-849 and 4-chloro-5-iodo-7H-pyrrolo[2,3-d]pyrimidine (6.97 g) in tetrahydrofuran (35 ml) was slowly added thereto. After the reaction mixture was stirred at room temperature for 2 hours, the solvent was distilled off under reduced pressure. The resulting residue was purified by silica gel column chromatography (developing solvent: hexane/ethyl acetate) to obtain the title compound (20.84 g) as a light-yellow, oily substance.

ESI-MS m/z 448,450 (MH$^+$).

Step 2

Synthesis of (S)-tert-butyl (1-(4-amino-5-iodo-7H-pyrrolo[2,3-d]pyrimidin-7-yl)but-3-en-2-yl)carbamate

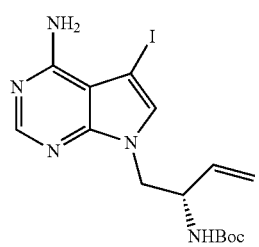

[Chem. 51]

An 8 N ammonia methanol solution (89.4 ml) was added to the (S)-tert-butyl (1-(4-chloro-5-iodo-7H-pyrrolo[2,3-d]pyrimidin-7-yl)but-3-en-2-yl)carbamate (20.84 g) obtained in Step 1, and the mixture was stirred in an autoclave at 120° C. for 6 hours. The reaction mixture was cooled with ice, and the solvent was distilled off under reduced pressure. After the resulting residue was diluted with a small amount of methanol, the resulting precipitate was collected by filtration, washed with cold methanol (11 ml), and then dried under reduced pressure to obtain the title compound (8.28 g) as a milky-white solid.

ESI-MS m/z 430 (MH$^+$).

Step 3

Synthesis of (S)-tert-butyl (1-(4-amino-5-(quinolin-3-yl)-7H-pyrrolo[2,3-d]pyrimidin-7-yl)but-3-en-2-yl)carbamate

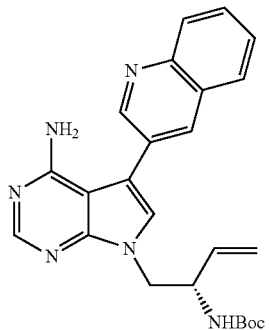

[Chem. 52]

A mixture of (S)-tert-butyl (1-(4-amino-5-iodo-7H-pyrrolo[2,3-d]pyrimidin-7-yl)but-3-en-2-yl)carbamate (8.26 g) obtained in Step 2, 3-quinolineboronic acid (4.99 g), cesium carbonate (12.54 g), 1,1'-bis(diphenylphosphino)ferrocene-palladium(II)dichloride (785.6 mg), DME (66 ml), and water (33 ml) was stirred under a nitrogen atmosphere at 100° C. for 2 hours. After cooling the reaction mixture, water and ethyl acetate were added thereto to separate the organic layer. The aqueous layer was then extracted with ethyl acetate twice. The resulting organic layer was dried over anhydrous magnesium sulfate, and the solvent was distilled off under reduced pressure. The resulting residue was purified by silica gel column chromatography (developing solvent: hexane/ethyl acetate, ethyl acetate/methanol) to obtain the title compound (8.0 g) as a light-orange solid.

ESI-MS m/z 431 (MH$^+$).

Step 4

Synthesis of (S)-tert-butyl (1-(4-amino-6-bromo-5-(quinolin-3-yl)-7H-pyrrolo[2,3-d]pyrimidin-7-yl)but-3-en-2-yl)carbamate

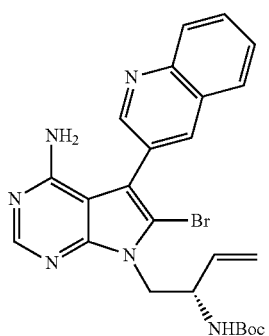

[Chem. 53]

N-Bromosuccinimide (3.63 g) was added to a solution of (S)-tert-butyl (1-(4-amino-5-(quinolin-3-yl)-7H-pyrrolo[2,3-d]pyrimidin-7-yl)but-3-en-2-yl)carbamate (7.98 g)

obtained in Step 3 in DMF (64 ml) at −15° C., and the mixture was stirred at −15° C. for 1 hour. A 10% aqueous sodium thiosulfate solution and ethyl acetate were added to the reaction mixture, and stirred at room temperature for 10 minutes. The organic layer was separated, and the aqueous layer was extracted with ethyl acetate twice. The resulting organic layer was washed with a saturated sodium chloride solution twice, and dried over anhydrous magnesium sulfate. The solvent was distilled off under reduced pressure. The resulting residue was purified by silica gel column chromatography (developing solvent: ethyl acetate/methanol) to obtain the title compound (6.30 g) as a light-brown solid.

$^1$H-NMR (CDCl$_3$) δ: 1.26 (9H, s), 4.35-4.39 (1H, m), 4.50-4.56 (1H, m), 4.72 (1H, brs), 4.92 (1H, brs), 5.26 (2H, d, J=10.5 Hz), 5.33-5.39 (1H, m), 5.92 (1H, ddd, J=17.2, 10.6, 5.4 Hz), 7.63-7.67 (1H, m), 7.79-7.83 (1H, m), 7.90-7.92 (1H, m), 8.19 (1H, d, J=8.3 Hz), 8.27 (1H, d, J=1.7 Hz), 8.35 (1H, s), 9.07 (1H, d, J=2.2 Hz).

ESI-MS m/z 509,511 (MH$^+$).

Reference Example 2

(R)-tert-Butyl (1-(4-amino-6-bromo-5-(quinolin-3-yl)-7H-pyrrolo[2,3-d]pyrimidin-7-yl)but-3-en-2-yl)carbamate

[Chem. 54]

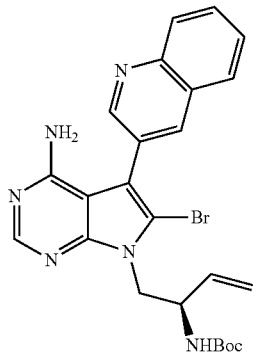

Step 1

Synthesis of (R)-tert-butyl (1-(4-chloro-5-iodo-7H-pyrrolo[2,3-d]pyrimidin-7-yl)but-3-en-2-yl)carbamate

[Chem. 55]

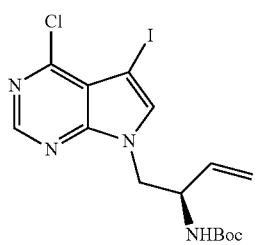

In accordance with Step 1 in Reference Example 1, except that (R)-tert-butyl (1-hydroxybut-3-en-2-yl)carbamate (8.74 g) was used in place of the (S)-tert-butyl (1-hydroxybut-3-en-2-yl)carbamate obtained in Step 1 in Reference Example 1, the title compound (11.05 g) was obtained as a white solid.

ESI-MS m/z 448,450 (MH$^+$).

Step 2

Synthesis of (R)-tert-butyl (1-(4-amino-6-bromo-5-(quinolin-3-yl)-7H-pyrrolo[2,3-d]pyrimidin-7-yl)but-3-en-2-yl)carbamate

[Chem. 56]

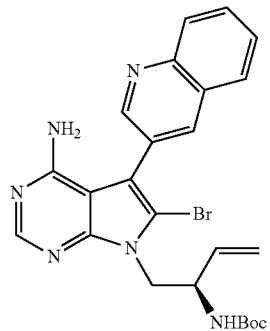

In accordance with Steps 2 to 4 in Reference Example 1, except that the (R)-tert-butyl (1-(4-chloro-5-iodo-7H-pyrrolo[2,3-d]pyrimidin-7-yl)but-3-en-2-yl)carbamate (7.88 g) obtained in Step 1 was used in place of the (S)-tert-butyl (1-(4-chloro-5-iodo-7H-pyrrolo[2,3-d]pyrimidin-7-yl)but-3-en-2-yl)carbamate obtained in Step 2 in Reference Example 1, the title compound (6.80 g) was obtained as a yellow solid.

$^1$H-NMR (CDCl$_3$) δ: 1.26 (9H, s), 4.35-4.39 (1H, m), 4.50-4.56 (1H, m), 4.72 (1H, brs), 4.92 (1H, brs), 5.26 (2H, d, J=10.5 Hz), 5.33-5.39 (1H, m), 5.92 (1H, ddd, J=17.2, 10.6, 5.4 Hz), 7.63-7.67 (1H, m), 7.79-7.83 (1H, m), 7.90-7.92 (1H, m), 8.19 (1H, d, J=8.3 Hz), 8.27 (1H, d, J=1.7 Hz), 8.35 (1H, s), 9.07 (1H, d, J=2.2 Hz).

ESI-MS m/z 509,511 (MH$^+$).

Reference Example 3

(S)-tert-Butyl (1-(4-amino-6-bromo-5-(quinolin-3-yl)-7H-pyrrolo[2,3-d]pyrimidin-7-yl)penta-4-en-2-yl)carbamate

[Chem. 57]

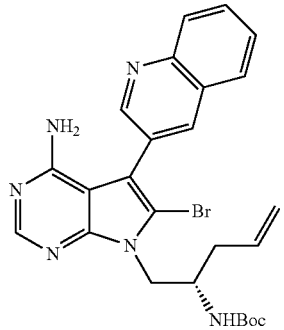

Step 1

Synthesis of (S)-tert-butyl (1-(4-chloro-5-iodo-7H-pyrrolo[2,3-d]pyrimidin-7-yl)penta-4-en-2-yl)carbamate

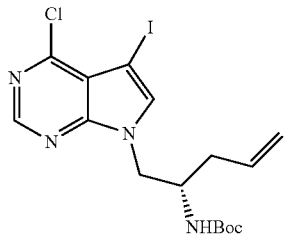

[Chem. 58]

In accordance with Step 1 in Reference Example 1, except that (S)-tert-butyl (1-hydroxypenta-4-en-2-yl)carbamate (11.93 g) was used in place of the (S)-tert-butyl (1-hydroxybut-3-en-2-yl)carbamate obtained in Step 1 in Reference Example 1, the title compound (4.96 g) was obtained as a yellow-brown, oily substance.

$^1$H-NMR (CDCl$_3$) δ: 1.35 (9H, s), 2.18-2.35 (2H, m), 3.97-4.05 (1H, m), 4.27-4.33 (1H, m), 4.40-4.45 (1H, m), 4.63-4.65 (1H, m), 5.14-5.19 (2H, m), 5.76-5.86 (1H, m), 7.42 (1H, brs), 8.62 (1H, s).

ESI-MS m/z 462, 464 (MH$^+$).

Step 2

Synthesis of (S)-tert-butyl (1-(4-amino-6-bromo-5-(quinolin-3-yl)-7H-pyrrolo[2,3-d]pyrimidin-7-yl)penta-4-en-2-yl)carbamate

[Chem. 59]

In accordance with Steps 2 to 4 in Reference Example 1, except that the (S)-tert-butyl (1-(4-chloro-5-iodo-7H-pyrrolo[2,3-d]pyrimidin-7-yl)penta-4-en-2-yl)carbamate (4.90 g) obtained in Step 1 was used in place of the (S)-tert-butyl (1-(4-chloro-5-iodo-7H-pyrrolo[2,3-d]pyrimidin-7-yl)but-3-en-2-yl)carbamate obtained in Step 2 in Reference Example 1, the title compound (3.67 g) was obtained as a light-yellow solid.

$^1$H-NMR (CDCl$_3$) δ: 1.23 (9H, s), 2.39-2.42 (2H, m), 4.19-4.27 (1H, m), 4.29-4.34 (1H, m), 4.43-4.50 (1H, m), 4.92 (2H, brs), 5.04 (1H, d, J=8.5 Hz), 5.18-5.24 (2H, m), 5.86-5.96 (1H, m), 7.63-7.67 (1H, m), 7.79-7.83 (1H, m), 7.90-7.92 (1H, m), 8.19 (1H, d, J=8.5 Hz), 8.27 (1H, d, J=1.5 Hz), 8.34 (1H, s), 9.07 (1H, d, J=2.0 Hz). ESI-MS m/z 523, 525 (MH$^+$).

Reference Example 4

(R)-tert-Butyl (1-(4-amino-6-bromo-5-(quinolin-3-yl)-7H-pyrrolo[2,3-d]pyrimidin-7-yl)penta-4-en-2-yl)carbamate

[Chem. 60]

Step 1

Synthesis of (R)-tert-butyl (1-(4-chloro-5-iodo-7H-pyrrolo[2,3-d]pyrimidin-7-yl)penta-4-en-2-yl)carbamate

[Chem. 61]

In accordance with Step 1 in Reference Example 1, except that (R)-tert-butyl (1-hydroxypenta-4-en-2-yl)carbamate (856.4 mg) was used in place of (S)-tert-butyl (1-hydroxybut-3-en-2-yl)carbamate in Step 1 in Reference Example 1, the title compound (1.54 g) was obtained as a milky-white solid.

$^1$H-NMR (CDCl$_3$) δ: 1.35 (9H, s), 2.18-2.35 (2H, m), 3.97-4.05 (1H, m), 4.27-4.33 (1H, m), 4.40-4.45 (1H, m), 4.63-4.65 (1H, m), 5.14-5.19 (2H, m), 5.76-5.86 (1H, m), 7.42 (1H, brs), 8.62 (1H, s).

ESI-MS m/z 462, 464 (MH$^+$).

Step 2

Synthesis of (R)-tert-butyl (1-(4-amino-6-bromo-5-(quinolin-3-yl)-7H-pyrrolo[2,3-d]pyrimidin-7-yl)penta-4-en-2-yl)carbamate

[Chem. 62]

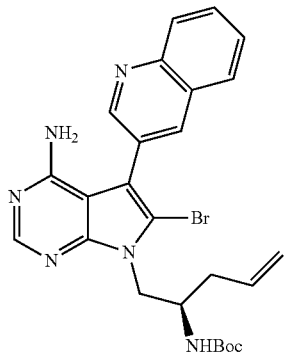

In accordance with Steps 2 to 4 in Reference Example 1, except that the (R)-tert-butyl (1-(4-chloro-5-iodo-7H-pyrrolo[2,3-d]pyrimidin-7-yl)penta-4-en-2-yl)carbamate (974.9 mg) obtained in Step 1 was used in place of the (S)-tert-butyl (1-(4-chloro-5-iodo-7H-pyrrolo[2,3-d]pyrimidin-7-yl)but-3-en-2-yl)carbamate obtained in Step 2 in Reference Example 1, the title compound (1.02 g) was obtained as a light-brown solid.

$^1$H-NMR (CDCl$_3$) δ: 1.23 (9H, s), 2.39-2.42 (2H, m), 4.19-4.27 (1H, m), 4.29-4.34 (1H, m), 4.43-4.50 (1H, m), 4.92 (2H, brs), 5.04 (1H, d, J=8.5 Hz), 5.18-5.24 (2H, m), 5.86-5.96 (1H, m), 7.63-7.67 (1H, m), 7.79-7.83 (1H, m), 7.90-7.92 (1H, m), 8.19 (1H, d, J=8.5 Hz), 8.27 (1H, d, J=1.5 Hz), 8.34 (1H, s), 9.07 (1H, d, J=2.0 Hz).

ESI-MS m/z 523,525 (MH$^+$).

Reference Example 5

(R)-tert-Butyl (5-(4-amino-6-bromo-5-(quinolin-3-yl)-7H-pyrrolo[2,3-d]pyrimidin-7-yl)penta-1-en-3-yl)carbamate

[Chem. 63]

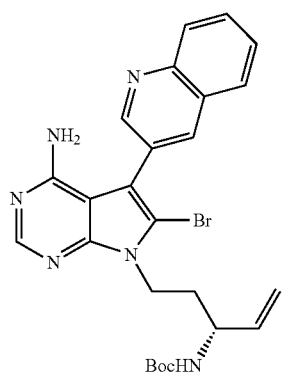

Step 1

Synthesis of (R)-tert-Butyl (5-(4-chloro-5-iodo-7H-pyrrolo[2,3-d]pyrimidin-7-yl)penta-1-en-3-yl)carbamate

[Chem. 64]

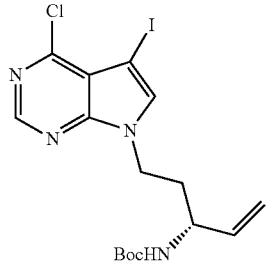

In accordance with Step 1 in Reference Example 1, except that (S)-tert-butyl (5-hydroxypenta-1-en-3-yl)carbamate (2.5 g) was used in place of the (S)-tert-butyl (1-hydroxybut-3-en-2-yl)carbamate obtained in Step 1 in Reference Example 1, the title compound (3.49 g) was obtained as a light-yellow solid.

ESI-MS m/z 463,465 (MH$^+$).

Step 2

Synthesis of (R)-tert-Butyl (5-(4-amino-6-bromo-5-(quinolin-3-yl)-7H-pyrrolo[2,3-d]pyrimidin-7-yl)penta-1-en-3-yl)carbamate

[Chem. 65]

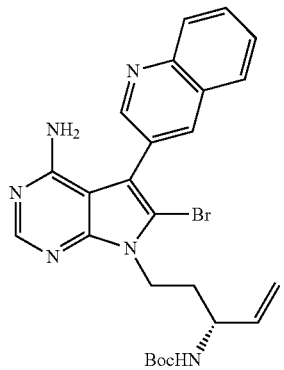

In accordance with Steps 2 to 4 in Reference Example 1, except that the (R)-tert-butyl (5-(4-chloro-5-iodo-7H-pyrrolo[2,3-d]pyrimidin-7-yl)penta-1-en-3-yl)carbamate (3.21 g) obtained in Step 1 was used in place of the (S)-tert-butyl (1-(4-chloro-5-iodo-7H-pyrrolo[2,3-d]pyrimidin-7-yl)but-3-en-2-yl)carbamate obtained in Step 2 in Reference Example 1, the title compound (3.15 g) was obtained as a light-brown solid.

$^1$H-NMR (CDCl$_3$) δ: 1.46 (9H, s), 2.02-2.21 (2H, m), 4.26-4.53 (3H, m), 4.90 (2H, brs), 5.07 (1H, d, J=12.4 Hz), 5.15 (1H, d, J=17.2 Hz), 5.15-5.23 (1H, m), 5.78 (1H, ddd, J=17.2, 12.4, 5.2 Hz), 7.61-7.67 (1H, m), 7.78-7.83 (1H, m), 7.88-7.93 (1H, m), 8.17-8.21 (1H, m), 8.26 (1H, d, J=2.2 Hz), 8.35 (1H, s), 9.06 (1H, d, J=2.2 Hz).

ESI-MS m/z 523, 525 (MH$^+$).

Reference Example 6

(R)-6-Bromo-7-(2-((tert-butyldimethylsilyl)oxy)but-3-en-1-yl)-5-(quinolin-3-yl)-7H-pyrrolo[2,3-d]pyrimidin-4-amine

[Chem. 66]

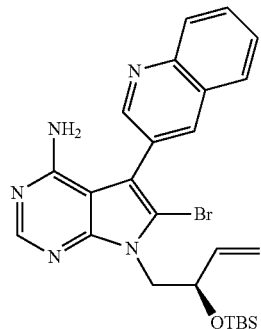

Step 1

Synthesis of 4-chloro-5-iodo-7-((2-(trimethylsilyl)ethoxy)methyl)-7H-pyrrolo[2,3-d]pyrimidine

[Chem. 67]

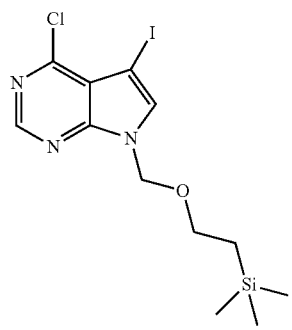

A solution of 4-chloro-5-iodo-7H-pyrrolo[2,3-d]pyrimidine (20.0 g) in DMF (50 ml) was slowly added to a solution of sodium hydride (3.4 g) in DMF (190 ml) under ice cooling. Thereafter, 2-(trimethylsilyl)ethoxymethyl chloride (13.3 ml) was added thereto, and stirred at the same temperature for 2 hours. 2-(Trimethylsilyl)ethoxymethyl chloride (1.3 ml) was additionally added to the reaction mixture, and stirred at room temperature for 1 hour. The reaction mixture was poured into water (600 ml), and stirred at room temperature for 15 minutes. The resulting precipitate was collected by filtration and washed with water and diisopropyl ether, followed by dissolution with ethyl acetate again. Insoluble matter was then filtered off by filtration. The solvent of the filtrate was distilled off under reduced pressure. Heptane was added to the resulting residue to collect the precipitate by filtration. The precipitate was washed with heptane, and dried under reduced pressure to obtain the title compound (21.2 g) as a white solid.

ESI-MS m/z 409,411 (MH$^+$).

Step 2

Synthesis of 5-iodo-7-((2-(trimethylsilyl)ethoxy)methyl)-7H-pyrrolo[2,3-d]pyrimidin-4-amine

[Chem. 68]

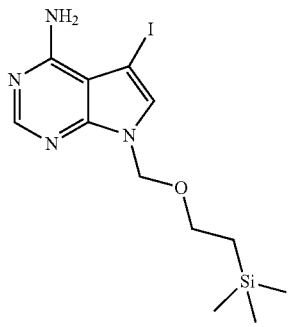

An 8 N ammonia methanol solution (120 ml) was added to the 4-chloro-5-iodo-7-((2-(trimethylsilyl)ethoxy)methyl)-7H-pyrrolo[2,3-d]pyrimidine (20.0 g) obtained in Step 1, and the mixture was stirred in a microwave reactor at 120° C. for 1 hour. After being cooled, the reaction mixture was diluted with methanol (65 ml) and water (185 ml). The resulting precipitate was collected by filtration, washed with water, and dried under reduced pressure to obtain the title compound (15.2 g) as a white solid.

ESI-MS m/z 391 (MH$^+$).

Step 3

Synthesis of 5-(quinolin-3-yl)-7-((2-(trimethylsilyl)ethoxy)methyl)-7H-pyrrolo[2,3-d]pyrimidin-4-amine

[Chem. 69]

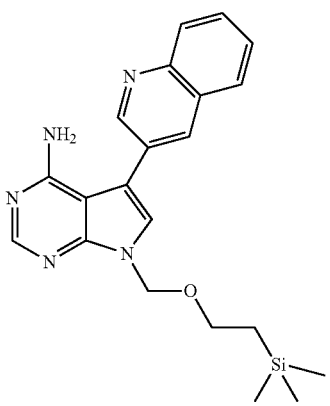

A 2 M sodium carbonate aqueous solution (38 ml) was added to a solution of 5-iodo-7-((2-(trimethylsilyl)ethoxy)methyl)-7H-pyrrolo[2,3-d]pyrimidin-4-amine (15.0 g) obtained in Step 2,3-quinolineboronic acid (8.6 g), and tetrakis triphenyl phosphine palladium(0) (2.2 g) in DME (270 ml), and stirred under a nitrogen atmosphere at 90° C. for 6 hours. After the reaction mixture was cooled, water (300 ml) was added thereto. The resulting precipitate was collected by filtration, then washed with water and diisopropyl ether, and dried under reduced pressure. The resulting residue was purified by silica gel column chromatography (developing solvent: methanol/chloroform) to obtain the title compound (10.17 g) as a light-yellow solid.

ESI-MS m/z 392 (MH⁺).

Step 4

Synthesis of 5-(quinolin-3-yl)-7H-pyrrolo[2,3-d]pyrimidin-4-amine hydrochloride

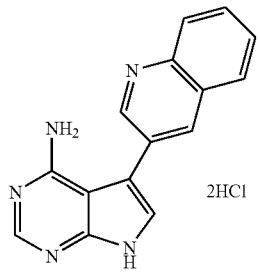

[Chem. 70]

2HCl

Concentrated hydrochloric acid (20 ml) was added at 90° C. to a solution of 5-(quinolin-3-yl)-7-((2-(trimethylsilyl)ethoxy)methyl)-7H-pyrrolo[2,3-d]pyrimidin-4-amine (10.0 g) obtained in Step 3 in ethanol (200 ml), and the mixture was stirred at the same temperature for 25 minutes. Subsequently, concentrated hydrochloric acid (30 ml) was added thereto, and the mixture was stirred at the same temperature for 75 minutes. After the reaction mixture was cooled, ethanol (100 ml) was added thereto, and stirred at 95° C. for 90 minutes. Subsequently, ethanol (100 ml) and concentrated hydrochloric acid (25 ml) were added, and the mixture was stirred at the same temperature for 4 days. After the reaction mixture was cooled, ethyl acetate was added thereto. The resulting precipitate was then collected by filtration, washed with ethyl acetate, and dried under reduced pressure to obtain the title compound (4.4 g) as a yellow solid.

ESI-MS m/z 335 (MH⁺).

Step 5

Synthesis of (R)-7-(2-((tert-butyldimethylsilyl)oxy)but-3-en-1-yl)-5-(quinolin-3-yl)-7H-pyrrolo[2,3-d]pyrimidin-4-amine

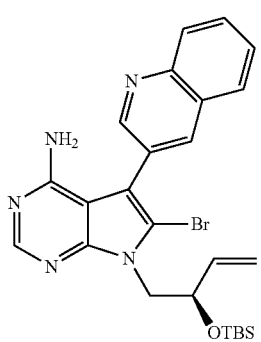

[Chem. 71]

Potassium carbonate (4.0 g) and (R)-2-((tert-butyldimethylsilyl)oxy)but-3-en-1-yl 4-methylbenzenesulfonate (1.43 g) were added to a solution of 5-(quinolin-3-yl)-7H-pyrrolo[2,3-d]pyrimidin-4-amine hydrochloride (1.22 g) obtained in Step 4 in DMF (12.2 ml) at room temperature, and the mixture was stirred at 90° C. for 20 hours. After the reaction mixture was cooled, water (49 ml) was added thereto, and the resulting mixture was stirred at room temperature for 3 hours. The resulting precipitate was collected by filtration, washed with water, and dried under reduced pressure. The resulting residue was purified by silica gel column chromatography (developing solvent: methanol/ethyl acetate) to obtain the title compound (1.31 g) as a light-yellow solid.

¹H-NMR (CDCl₃) δ: −0.32 (3H, s), −0.11 (3H, s), 0.80 (9H, s), 4.06 (1H, dd, J=13.9, 8.5 Hz), 4.46 (1H, dd, J=13.9, 3.2 Hz), 4.59-4.64 (1H, m), 5.06 (2H, brs), 5.22 (1H, d, J=10.5 Hz), 5.40 (1H, d, J=16.8 Hz), 5.89-5.97 (1H, m), 7.21 (1H, s), 7.61-7.65 (1H, m), 7.74-7.78 (1H, m), 7.89 (1H, d, J=8.1 Hz), 8.17 (1H, d, J=8.3 Hz), 8.23 (1H, d, J=2.2 Hz), 8.40 (1H, s), 9.10 (1H, d, J=2.0 Hz).

ESI-MS m/z 446 (MH⁺).

Step 6

Synthesis of (R)-6-bromo-7-(2-((tert-butyldimethylsilyl)oxy)but-3-en-1-yl)-5-(quinolin-3-yl)-7H-pyrrolo[2,3-d]pyrimidin-4-amine

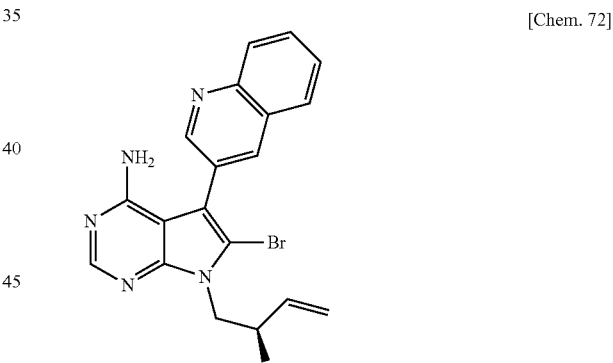

[Chem. 72]

In accordance with Step 4 in Reference Example 1, except that the (R)-7-(2-((tert-butyldimethylsilyl)oxy)but-3-en-1-yl)-5-(quinolin-3-yl)-7H-pyrrolo[2,3-d]pyrimidin-4-amine (1.30 g) obtained in Step 5 was used in place of (S)-tert-butyl (1-(4-amino-5-(quinolin-3-yl)-7H-pyrrolo[2,3-d]pyrimidin-7-yl)but-3-en-2-yl)carbamate in Step 4 in Reference Example 1, the title compound (1.44 g) was obtained as a yellow solid.

¹H-NMR (CDCl₃) δ: −0.34 (3H, s), −0.12 (3H, s), 0.75 (9H, s), 4.33-4.40 (2H, m), 4.74-4.79 (1H, dm), 4.91 (2H, brs), 5.21-5.24 (1H, m), 5.36-5.41 (1H, m), 5.92-6.01 (1H, m), 7.63-7.67 (1H, m), 7.79-7.83 (1H, m), 7.92 (1H, d, J=7.8 Hz), 8.20 (1H, d, J=8.5 Hz), 8.24 (1H, d, J=2.2 Hz), 8.37 (1H, s), 9.06 (1H, d, J=2.2 Hz).

ESI-MS m/z 524, 526 (MH+).

Example 10

(S)-tert-Butyl (4-amino-5-(quinolin-3-yl)-6,7,8,9-tetrahydropyrimido[5,4-b]indolizin-8-yl)carbamate

[Chem. 73]

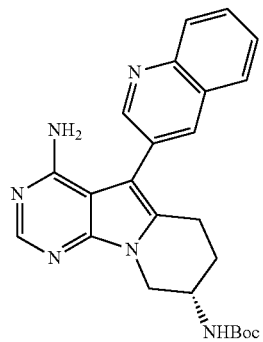

A solution of 0.5 M 9-borabicyclo[3.3.1]nonane in tetrahydrofuran (141.3 ml) was added to a solution of (S)-tert-butyl (1-(4-amino-6-bromo-5-(quinolin-3-yl)-7H-pyrrolo[2,3-d]pyrimidin-7-yl)but-3-en-2-yl)carbamate (6.0 g) obtained in Reference Example 1 in tetrahydrofuran (42 ml) under a nitrogen atmosphere at room temperature, and stirred at room temperature for 2 hours. A 2 N sodium hydroxide aqueous solution (84.8 ml) was slowly added to the reaction mixture at room temperature, and degassed under reduced pressure. Under a nitrogen atmosphere, (tetrakistriphenylphosphine)palladium(0) (1.70 g) was added thereto, and the mixture was stirred at 66° C. for 12 hours. After the reaction mixture was cooled, the organic layer was separated and washed with a 20% ammonium chloride aqueous solution (60 ml). SH silica gel (6.0 g) was then added to the organic layer, and the result was stirred at 50° C. under a nitrogen atmosphere for 14 hours, and then filtered. SH silica gel (produced by Fuji Silysia Chemical Ltd.) (6.0 g) was added to the filtrate again, and the result was stirred under a nitrogen atmosphere at 50° C. for 14 hours, and then filtered. The solvent was distilled off from the filtrate under reduced pressure. The resulting residue was purified by silica gel column chromatography (developing solvent: ethyl acetate/methanol) to obtain the title compound (4.46 g) (yield: 88%) as a light-yellow solid.

$^1$H-NMR (CDCl$_3$) δ: 1.48 (9H, s), 1.91-2.00 (1H, m), 2.12-2.19 (1H, m), 2.98-3.11 (2H, m), 4.00 (1H, dd, J=12.7, 7.1 Hz), 4.32 (1H, brs), 4.55 (1H, dd, J=12.7, 4.6 Hz), 4.81-4.83 (1H, m), 4.90 (2H, brs), 7.61-7.65 (1H, m), 7.75-7.80 (1H, m), 7.88 (1H, d, J=8.0 Hz), 8.16-8.18 (2H, m), 8.33 (1H, s), 9.02 (1H, d, J=2.2 Hz). ESI-MS m/z 431 (MH$^+$).

Example 11

9-Borabicyclo[3.3.1]nonane dimer (0.431 g) was added to a solution of (S)-tert-butyl (1-(4-amino-6-bromo-5-(quinolin-3-yl)-7H-pyrrolo[2,3-d]pyrimidin-7-yl)but-3-en-2-yl)carbamate (0.3 g) obtained in Reference Example 1 in tetrahydrofuran (4.5 ml) under a nitrogen atmosphere at room temperature, and the mixture was stirred at room temperature for 2 hours. A 4 N sodium hydroxide aqueous solution (2.12 ml) was slowly added to the reaction mixture at room temperature, and degassed under reduced pressure. Under a nitrogen atmosphere, (tetrakistriphenylphosphine)palladium(0) (0.136 g) was added to the resulting mixture, and stirred at 64° C. for 12 hours. After the reaction mixture was cooled, and diluted with ethyl acetate, a saturated ammonium chloride aqueous solution was added thereto. After the insoluble matter resulting in this stage was removed by filtration, the organic layer was separated. The resulting organic layer was dried over anhydrous sodium sulfate, then filtered, and concentrated under reduced pressure to obtain a crude product. The crude product was purified by silica gel column chromatography (developing solvent: ethyl acetate/methanol) to obtain (S)-tert-butyl (4-amino-5-(quinolin-3-yl)-6,7,8,9-tetrahydropyrimido[5,4-b]indolizin-8-yl)carbamate (203 mg) (yield: 80%) as a light-yellow solid.

Example 12

9-Borabicyclo[3.3.1]nonane dimer (431 mg) was added to a solution of (S)-tert-butyl (1-(4-amino-6-bromo-5-(quinolin-3-yl)-7H-pyrrolo[2,3-d]pyrimidin-7-yl)but-3-en-2-yl)carbamate (300 mg) obtained in Reference Example 1 in 1,2-dimethoxyethane (4.5 ml) under a nitrogen atmosphere at room temperature, and the mixture was stirred at 48° C. for 40 minutes. After the mixture was allowed to cool to room temperature, a 4 N sodium hydroxide aqueous solution (2.1 ml) was slowly added to the reaction mixture at room temperature, and degassed under reduced pressure. Under a nitrogen atmosphere, (tetrakistriphenylphosphine)palladium(0) (136 mg) was added thereto, and stirred at 79° C. for 5 hours. After the reaction mixture was cooled, and diluted with ethyl acetate, a saturated ammonium chloride aqueous solution was added. The insoluble matter resulting in this stage was removed by filtration, and the organic layer was separated. The resulting organic layer was dried over anhydrous sodium sulfate and filtered, and then concentrated under reduced pressure to obtain a crude product. The crude product was purified by silica gel column chromatography (developing solvent: ethyl acetate/methanol) to obtain (S)-tert-butyl (4-amino-5-(quinolin-3-yl)-6,7,8,9-tetrahydropyrimido[5,4-b]indolizin-8-yl)carbamate (0.190 g) (yield: 75%) as a light-yellow solid.

Example 13

In accordance with Example 10, except that a 4 N lithium hydroxide aqueous solution (1.8 ml) was used in place of the sodium hydroxide aqueous solution used in Example 10, (S)-tert-butyl (4-amino-5-(quinolin-3-yl)-6,7,8,9-tetrahydropyrimido[5,4-b]indolizin-8-yl)carbamate (224 mg) (yield: 88%) was obtained as a light-yellow solid.

Example 14

In accordance with Example 10, except that a 4 N potassium hydroxide aqueous solution (1.8 ml) was used in place of the sodium hydroxide aqueous solution used in Example 10, (S)-tert-butyl (4-amino-5-(quinolin-3-yl)-6,7,8,9-tetrahydropyrimido[5,4-b]indolizin-8-yl)carbamate (198 mg) (yield: 78%) was obtained as a light-yellow solid.

Example 15

In accordance with Example 10, except that a 4 N cesium hydroxide aqueous solution (1.8 ml) was used in place of the sodium hydroxide aqueous solution used in Example 10, (S)-tert-butyl (4-amino-5-(quinolin-3-yl)-6,7,8,9-tetrahydropyrimido[5,4-b]indolizin-8-yl)carbamate (202 mg) (yield: 80%) was obtained as a light-yellow solid.

Example 16

In accordance with Example 10, except that tris(dibenzylideneacetone)dipalladium(0) (34 mg) and triphenylphosphine (39 mg) were used in place of the (tetrakistriphenylphosphine)palladium(0) used in Example 10, (S)-tert-butyl (4-amino-5-(quinolin-3-yl)-6,7,8,9- tetrahydropyrimido[5,4-b]indolizin-8-yl)carbamate (194 mg) (yield: 76%) was obtained as a light-yellow solid.

Example 17

(R)-tert-butyl (4-amino-5-(quinolin-3-yl)-6,7,8,9-tetrahydropyrimido[5,4-b]indolizin-8-yl)carbamate

[Chem. 74]

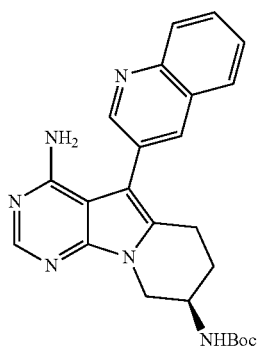

In accordance with Example 10, except that the (R)-tert-butyl (1-(4-amino-6-bromo-5-(quinolin-3-yl)-7H-pyrrolo[2,3-d]pyrimidin-7-yl)but-3-en-2-yl)carbamate (6.70 g) obtained in Reference Example 2 was used in place of the (S)-tert-butyl (1-(4-amino-6-bromo-5-(quinolin-3-yl)-7H-pyrrolo[2,3-d]pyrimidin-7-yl)but-3-en-2-yl)carbamate obtained in Example 10, (R)-tert-butyl (4-amino-5-(quinolin-3-yl)-6,7,8,9-tetrahydropyrimido[5,4-b]indolizin-8-yl)carbamate (4.76 g) (yield: 84%) was obtained as a light-yellow solid.

$^1$H-NMR (CDCl$_3$) δ: 1.48 (9H, s), 1.91-2.00 (1H, m), 2.12-2.19 (1H, m), 2.98-3.11 (2H, m), 4.00 (1H, dd, J=12.7, 7.1 Hz), 4.32 (1H, brs), 4.55 (1H, dd, J=12.7, 4.6 Hz), 4.81-4.83 (1H, m), 4.90 (2H, brs), 7.61-7.65 (1H, m), 7.75-7.80 (1H, m), 7.88 (1H, d, J=8.0 Hz), 8.16-8.18 (2H, m), 8.33 (1H, s), 9.02 (1H, d, J=2.2 Hz). ESI-MS m/z 431 (MH$^+$).

Example 18

(S)-tert-Butyl (4-amino-5-(quinolin-3-yl)-7,8,9,10-tetrahydro-6H-pyrimido[5',4':4,5]pyrrolo[1,2-a]azepin-9-yl)carbamate

[Chem. 75]

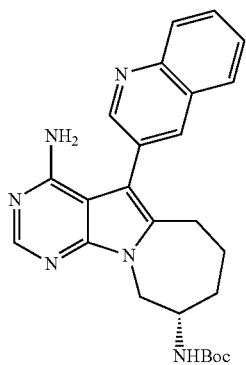

In accordance with Example 10, except that the (S)-tert-butyl (1-(4-amino-6-bromo-5-(quinolin-3-yl)-7H-pyrrolo[2,3-d]pyrimidin-7-yl)penta-4-en-2-yl)carbamate (2.0 g) obtained in Reference Example 8 was used in place of the (S)-tert-butyl (1-(4-amino-6-bromo-5-(quinolin-3-yl)-7H-pyrrolo[2,3-d]pyrimidin-7-yl)but-3-en-2-yl)carbamate obtained in Example 10, the title compound (1.56 g) (yield: 92%) was obtained as a light-yellow solid.

$^1$H-NMR (CDCl$_3$) δ: 1.43 (9H, s), 1.77-1.89 (2H, m), 1.95-2.14 (2H, m), 2.71-2.84 (1H, m), 2.86-3.00 (1H, m), 4.00-4.15 (1H, m), 4.24-4.40 (1H, m), 4.40-4.50 (1H, m), 4.84 (3H, brs), 7.62-7.66 (1H, m), 7.77-7.81 (1H, m), 7.89-7.91 (1H, m), 8.18-8.20 (2H, m), 8.33 (1H, s), 8.98 (1H, d, J=1.5 Hz).

ESI-MS m/z 445 (MH$^+$).

Example 19

(R)-tert-Butyl (4-amino-5-(quinolin-3-yl)-7,8,9,10-tetrahydro-6H-pyrimido[5',4':4,5]pyrrolo[1,2-a]azepin-9-yl)carbamate

[Chem. 76]

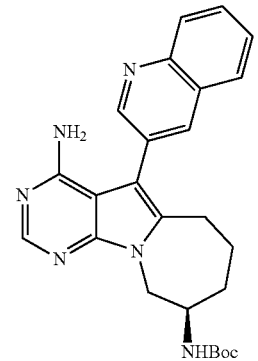

In accordance with Example 10, except that the (R)-tert-butyl (1-(4-amino-6-bromo-5-(quinolin-3-yl)-7H-pyrrolo[2,3-d]pyrimidin-7-yl)penta-4-en-2-yl)carbamate (690 mg) obtained in Reference Example 9 was used in place of the (S)-tert-butyl (1-(4-amino-6-bromo-5-(quinolin-3-yl)-7H-pyrrolo[2,3-d]pyrimidin-7-yl)but-3-en-2-yl)carbamate obtained in Example 10, the title compound (429 mg) (yield: 73%) was obtained as a yellow solid.

$^1$H-NMR (CDCl$_3$) δ: 1.43 (9H, s), 1.77-1.89 (2H, m), 1.95-2.14 (2H, m), 2.71-2.84 (1H, m), 2.86-3.00 (1H, m), 4.00-4.15 (1H, m), 4.24-4.40 (1H, m), 4.40-4.50 (1H, m), 4.84 (3H, brs), 7.62-7.66 (1H, m), 7.77-7.81 (1H, m), 7.89-7.91 (1H, m), 8.18-8.20 (2H, m), 8.33 (1H, s), 8.98 (1H, d, J=1.5 Hz).

ESI-MS m/z 445 (MH$^+$).

Example 20

(S)-tert-Butyl (4-amino-5-(quinolin-3-yl)-7,8,9,10-tetrahydro-6H-pyrimido[5',4':4,5]pyrrolo[1,2-a]azepin-8-yl)carbamate

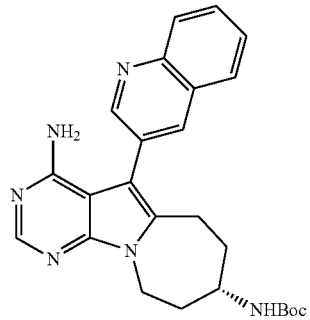

[Chem. 77]

In accordance with Example 10, except that the (R)-tert-butyl (5-(4-amino-6-bromo-5-(quinolin-3-yl)-7H-pyrrolo[2,3-d]pyrimidin-7-yl)penta-1-en-3-yl)carbamate (994 mg) obtained in Reference Example 10 was used in place of the (S)-tert-butyl (1-(4-amino-6-bromo-5-(quinolin-3-yl)-7H-pyrrolo[2,3-d]pyrimidin-7-yl)but-3-en-2-yl)carbamate obtained in Example 10, the title compound (439 mg) (yield: 52%) was obtained as a yellow solid.

$^1$H-NMR (CDCl$_3$) δ: 1.46 (9H, s), 2.18-2.28 (1H, m), 2.32-2.42 (1H, m), 2.65-2.77 (1H, m), 2.99-3.08 (1H, m), 3.80-3.97 (2H, m), 4.53-4.62 (1H, m), 4.80 (2H, brs), 4.97-5.11 (1H, m), 7.61-7.66 (1H, m), 7.76-7.81 (1H, m), 7.88 (1H, d, J=8.0 Hz), 8.15-8.20 (2H, m), 8.33 (1H, s), 8.97 (1H, d, J=2.2 Hz).

ESI-MS m/z 445 (MH$^+$).

Example 21

(R)-8-((tert-Butyldimethylsilyl)oxy)-5-(quinolin-3-yl)-6,7,8,9-tetrahydropyrimido[5,4-b]indolizin-4-amine

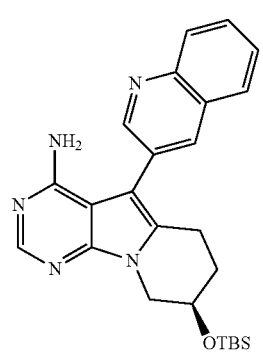

[Chem. 78]

In accordance with Example 10, except that the (R)-6-bromo-7-(2-((tert-butyldimethylsilyl)oxy)but-3-en-1-yl)-5-(quinolin-3-yl)-7H-pyrrolo[2,3-d]pyrimidin-4-amine (1.0 g) obtained in Reference Example 11 was used in place of the (S)-tert-butyl (1-(4-amino-6-bromo-5-(quinolin-3-yl)-7H-pyrrolo[2,3-d]pyrimidin-7-yl)but-3-en-2-yl)carbamate obtained in Example 10, (R)-8-((tert-butyldimethylsilyl)oxy)-5-(quinolin-3-yl)-6,7,8,9-tetrahydropyrimido[5,4-b]indolizin-4-amine (546 mg) (yield: 64%) was obtained.

$^1$H-NMR (CDCl$_3$) δ: 0.14 (3H, s), 0.15 (3H, s), 0.91 (9H, s), 1.97-2.02 (2H, m), 2.85-2.92 (2H, m), 3.14-3.22 (1H, m), 4.11-4.18 (1H, m), 4.28-4.33 (1H, m), 4.41-4.46 (1H, m), 4.95 (2H, brs), 7.61-7.65 (1H, m), 7.75-7.79 (1H, m), 7.88-7.90 (1H, m), 8.16-8.18 (2H, m), 8.35 (1H, s), 9.04 (1H, d, J=2.0 Hz).

ESI-MS m/z 446 (MH$^+$).

Reference Example 7

In accordance with Example 10, except that 1,1'-bis(diphenylphosphino)ferrocenepalladium(II)dichloride (32 mg) was used in place of the (tetrakistriphenylphosphine)palladium (0) used in Example 10, (S)-tert-butyl (4-amino-5-(quinolin-3-yl)-6,7,8,9-tetrahydropyrimido[5,4-b]indolizin-8-yl)carbamate (21 mg) (yield: 25%) was obtained as a light-yellow solid.

Reference Example 8

In accordance with Example 10, except that cesium carbonate (2.3 g) and water (1.8 ml) were used in place of the sodium hydroxide aqueous solution obtained in Example 10, (S)-tert-butyl (4-amino-5-(quinolin-3-yl)-6,7,8,9-tetrahydropyrimido[5,4-b]indolizin-8-yl)carbamate (88 mg) (yield: 35%) was obtained as a light-yellow solid.

Test Examples

The compounds of the present invention were tested by the following methods.

Test Example 1

Measurement of Inhibitory Activity for Various EGFR Kinases (In Vitro)

1) Measurement of EGFR (T790M/L858R) Kinase Inhibitory Activity

The inhibitory activities of the compounds I-1, I-2, I-3, I-4, I-5, I-6, I-7, I-8, and I-9 for EGFR (T790M/L858R) kinase were measured.

The materials were as follows. The substrate peptide was a biotinylated peptide (biotin-EEPLYWSFPAKKK) synthesized by reference to the amino acid sequence of FL-Peptide 22 (a reagent for LabChip® Series; Caliper Life Sciences, Inc.). The EGFR (T790M/L858R) was a purified recombinant human EGFR (T790M/L858R) protein purchased from Carna Biosciences, Inc.

The measurement method was as follows. The compounds I-1, I-2, I-3, I-4, I-5, I-6, I-7, I-8, and I-9 were each dissolved in dimethylsulfoxide (DMSO), and then each serially diluted with DMSO. Next, the EGFR (T790M/L858R) protein, substrate peptide (final concentration: 250 nM), magnesium chloride (final concentration: 10 mM), manganese chloride (final concentration: 10 mM), ATP (final concentration: 1 μM), and the diluted DMSO solution of each compound (final concentration of DMSO: 2.5%) were added to a kinase reaction buffer (Carna Biosciences, Inc.), and the mixture was incubated at 25° C. for 120 minutes for kinase reaction. EDTA was added thereto to a final concentration of 24 mM to thereby terminate the reaction. Then, a detection solution containing europium (Eu)-labeled anti-phosphorylated tyrosine antibody PT66 (PerkinElmer) and SureLight APC- SA (PerkinElmer) was added, and the resulting mixture was allowed to stand at room temperature for 2 hours or more. Finally, the intensity of fluorescence under the excitation light with a wavelength of 337 nm was measured by a PHERAstar FS (BMG LABTECH) at two wavelengths of 620 nm and 665 nm. The level of phosphorylation of each test sample was calculated from the fluorescence intensity ratio of the two wavelengths in DMSO control and in the test sample, and the compound concentration at which phosphorylation was inhibited by 50% was determined as the $IC_{50}$ value (nM) of each compound.

2) Measurement of EGFR (d746-750/T790M) Kinase Inhibitory Activity

The inhibitory activities of the compounds I-1, I-2, I-3, I-4, I-5, I-6, I-7, I-8, and I-9 for EGFR (d746-750/T790M) kinase were measured.

The materials were as follows. The EGFR (d746-750/T790M) was a purified recombinant human EGFR (d746-750/T790M) protein purchased from Carna Biosciences, Inc. The final concentration of ATP was 1.5 µM. As for other conditions, the same materials and methods as those used in the measurement of EGFR (T790M/L858R) kinase inhibitory activity were used to determine the $IC_{50}$ value (nM) of each compound.

3) Measurement of EGFR (L858R) Kinase Inhibitory Activity

The inhibitory activities of the compounds I-1, I-2, I-3, I-4, I-5, I-6, I-7, I-8, and I-9 for EGFR (L858R) kinase were measured.

The materials were as follows. The EGFR (L858R) was a purified recombinant human EGFR (L858R) protein purchased from Carna Biosciences, Inc. The final concentration of ATP was 4 µM. As for other conditions, the same materials and methods as those used in the measurement of EGFR (T790M/L858R) kinase inhibitory activity were used to determine the $IC_{50}$ value (nM) of each compound.

4) Measurement of EGFR (d746-750) Kinase Inhibitory Activity

The inhibitory activities of the compounds I-1, I-2, I-3, I-4, I-5, I-6, I-7, I-8, and I-9 for EGFR (d746-750) kinase activity were measured.

The materials were as follows. The EGFR (d746-750) was a purified recombinant human EGFR (d746-750) protein purchased from Carna Biosciences, Inc. The final concentration of ATP was 5 µM. The incubation time for the kinase reaction was 90 minutes. As for other conditions, the same materials and methods as those used in the measurement of EGFR (T790M/L858R) kinase inhibitory activity were used to determine the $IC_{50}$ value (nM) of each compound.

5) EGFR (WT)

The inhibitory activities of the compounds I-1, I-2, I-3, I-4, I-5, I-6, I-7, I-8, and I-9 on EGFR (WT) kinase were measured.

The materials were as follows. As the EGFR (WT), the cytoplasmic domain of human EGFR (WT) in which a FLAG tag was fused to the N-terminus was expressed in a baculovirus expression system using insect Sf9 cells, and purified with anti-FLAG antibody agarose (Sigma-Aldrich). The final concentration of the substrate peptide was 500 nM, and the final concentration of ATP was 4.7 µM. As for other conditions, the same materials and methods as those used in the measurement of EGFR (T790M/L858R) kinase inhibitory activity were used to determine the $IC_{50}$ value (nM) of each compound.

Table 1 shows the results.

It was confirmed that the compounds I-1, I-2, I-3, I-4, I-5, I-6, I-7, I-8, and I-9 showed potent inhibitory activities not only for EGFR (L858R) and EGFR (d746-750), but also for EGFR (T790M/L858R) and EGFR (d746-750/T790M). It was also confirmed that their inhibitory activities for EGFR (WT) were lower than those for the above mutant EGFR proteins.

In contrast, it was confirmed that N-(3-(4-amino-6,7,8,9-tetrahydropyrimide[5,4-b]indolizin-5-yl)phenyl)benzamide (PTL 1), which was a compound having a structure similar to that of the compound of the present invention, had almost no inhibitory activity for these EGFR kinases.

TABLE 1

| | Type of EGFR | | | | |
|---|---|---|---|---|---|
| Compound | EGFR (T790M/ L858R) | EGFR (d746-750/ T790M) | EGFR (L858R) | EGFR (d746- 750) | EGFR (WT) |
| I-1 | 5.3 | 2.8 | 14 | 13 | 170 |
| I-2 | 0.3 | 0.2 | 0.4 | 0.4 | 4.3 |
| I-3 | 1.3 | 0.6 | 1.3 | 1 | 18 |
| I-4 | 6.7 | 4.1 | 12 | 10 | 120 |
| I-5 | 0.4 | 0.3 | 0.7 | 0.5 | 5.9 |
| I-6 | 1.2 | 1.2 | 2.9 | 3.6 | 41 |
| I-7 | 1.4 | 0.5 | 2.9 | 1.8 | 33 |
| I-8 | 18 | 13 | 41 | 20 | 490 |
| I-9 | 160 | 82 | 350 | 270 | 3600 |
| Comp. Ex. 1 | >5000 | >5000 | >5000 | 1500 | >5000 |

Test Example 2

Measurement of Growth Inhibitory Activity for Wild Type and Mutant EGFR-Expressing Cell Lines (In Vitro)

1) A lung adenocarcinoma cell line NCI-H1975 expressing EGFR (T790M/L858R), 2) a lung adenocarcinoma cell line HCC827 expressing EGFR (d746-750), and 3) a human epidermoid carcinoma cell line A431 expressing EGFR (WT) were each suspended in the medium recommended by ATCC. The cell suspension was seeded in each well of a 384-well flat microplate or 96-well flat plate, and cultured in an incubator containing 5% carbon dioxide gas at 37° C. for one day. The compound of the present invention and the reference compound were dissolved in DMSO, and then the DMSO solution of each test compound was diluted with DMSO to a concentration 200 times higher than the final concentration. The diluted DMSO solution of the test compound was diluted with the medium used to suspend each cell line, and the diluted solution was added to each well of the cell culture plate so that the final concentration of DMSO was 0.5%. Then, the cells were cultured in an incubator containing 5% carbon dioxide gas at 37° C. for three days. The number of cells was measured at the time of initiation and termination of the culture by using a CellTiter-Glo Assay (produced by Promega) according to a protocol recommended by Promega. The cell growth inhibition rate was calculated by the following formula, and the concentration of the test compound at which the cell growth was inhibited by 50% ($GI_{50}$ (nM)) was determined.

Growth inhibition rate (%)=(C-T)/(C-C0)×100

T: Luminescence intensity of well to which test compound was added

C: Luminescence intensity of well to which test compound was not added

C0: Luminescence intensity of well measured before addition of test compound

Table 2 shows the results.

It was confirmed that the compounds I-2 and I-3 showed potent growth-inhibitory activities not only for the EGFR (d746-750)-expressing cells, but also for the EGFR (T790M/L858R)-expressing cells. It was also confirmed that the compounds I-2 and I-3 showed weaker growth-inhibitory activities for the EGFR (WT)-expressing cells than for the above cells expressing mutant EGFRs.

TABLE 2

| | Test Example 2 | | |
|---|---|---|---|
| | 1) | 2) | 3) |
| Type of EGFR | EGFR (T790M/L858R) | EGFR (d746-750) | EGFR (WT) |
| Cell name | NCI-H1975 | HCC827 | A431 |
| Compound | | | |
| I-2 | 27 | 5 | 590 |
| I-3 | 86 | 10 | 1800 |

The invention claimed is:

1. A compound represented by the following Formula (I)

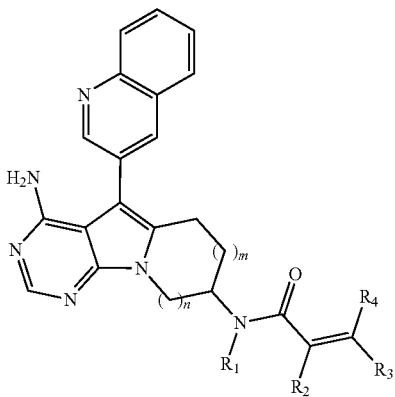

or a salt thereof,
wherein m is 1 or 2;
n is 1 or 2;
$R_1$ is a hydrogen atom or a $C_1$-$C_4$ alkyl group; and
$R_2$, $R_3$, and $R_4$ are the same or different, and are each a hydrogen atom, a halogen atom, a $C_1$-$C_4$ alkyl group, or a group represented by Formula (a):

—CH$_2$—N(R$_5$)(R$_6$)  (a)

wherein $R_5$ and $R_6$ are the same or different and each represents a hydrogen atom or a $C_1$-$C_4$ alkyl group, or $R_5$ and $R_6$ may form a heterocycloalkyl group having a 4 to 6 membered-ring, together with the nitrogen atom bound thereto.

2. The compound or a salt thereof according to claim 1, wherein m is 1 or 2;
n is 1 or 2;
$R_1$ is a hydrogen atom or a $C_1$-$C_4$ alkyl group; and
$R_2$, $R_3$, and $R_4$ are the same or different, and are each a hydrogen atom, a halogen atom, a $C_1$-$C_4$ alkyl group, or a group represented by Formula (a):

—CH$_2$—N(R$_5$)(R$_6$)  (a)

wherein $R_5$ and $R_6$ are the same or different and each represents a $C_1$-$C_4$ alkyl group.

3. The compound or a salt thereof according to claim 1, wherein
m is 1 or 2;
n is 1 or 2;
$R_1$ is a hydrogen atom or methyl group; and
$R_2$, $R_3$, and $R_4$ are the same or different, and are each a hydrogen atom, a chlorine atom, or a dimethylamino methyl group.

4. The compound or a salt thereof according to claim 1, wherein m and n are (m,n)=(1,1), (1,2), or (2,1).

5. The compound or a salt thereof according to claim 1, wherein the compound is selected from the following group of compounds:
(R)-N-(4-amino-5-(quinolin-3-yl)-6,7,8,9-tetrahydropyrimido[5,4-b]indolizin-8-yl)acrylamide,
(S)-N-(4-amino-5-(quinolin-3-yl)-6,7,8,9-tetrahydropyrimido[5,4-b]indolizin-8-yl)acrylamide,
N-(4-amino-5-(quinolin-3-yl)-6,7,8,9-tetrahydropyrimido[5,4-b]indolizin-8-yl)-N-methylacrylamide,
(E)-N-(4-amino-5-(quinolin-3-yl)-6,7,8,9-tetrahydropyrimido[5,4-b]indolizin-8-yl)-4-(dimethylamino)-2-butenamide,
(S,E)-N-(4-amino-5-(quinolin-3-yl)-6,7,8,9-tetrahydropyrimido[5,4-b]indolizin-8-yl)-3-chloroacrylamide,
(S,Z)-N-(4-amino-5-(quinolin-3-yl)-6,7,8,9-tetrahydropyrimido[5,4-b]indolizin-8-yl)-3-chloroacrylamide,
(S)-N-(4-amino-5-(quinolin-3-yl)-7,8,9,10-tetrahydro-6H-pyrimido[5',4':4,5]pyrrolo[1,2-a]azepin-8-yl)acrylamide,
(S)-N-(4-amino-5-(quinolin-3-yl)-7,8,9,10-tetrahydro-6H-pyrimido[5',4':4,5]pyrrolo[1,2-a]azepin-9-yl)acrylamide, and (R)-N-(4-amino-5-(quinolin-3-yl)-7,8,9,10-tetrahydro-6H-pyrimido[5',1':4,5]pyrrolo[1,2-a]azepin-9-yl)acrylamido.

6. An EGFR inhibitor comprising the compound or a salt thereof according to claim 1 as an active ingredient.

7. A pharmaceutical composition comprising the compound or a salt thereof according to claim 1.

8. An antitumor agent comprising the compound or a salt thereof according to claim 1 as an active ingredient.

9. A method for treating a cancer selected from the group consisting of head and neck cancer, colon cancer, rectum cancer and lung cancer, the method comprising a step of administering to the mammal the compound or a salt thereof according to claim 1 at a dose effective for treating the cancer.

* * * * *